United States Patent
Ohno et al.

(10) Patent No.: US 12,178,939 B2
(45) Date of Patent: Dec. 31, 2024

(54) INORGANIC SALT-PROTEIN COMPOSITE MEDICAL INSTRUMENT

(71) Applicants: Cell-Medicine, Inc., Ibaraki (JP); National Institute of Advanced Industrial Science and Technology, Tokyo (JP); University of Tsukuba, Ibaraki (JP); Nihon Parkerizing Co., Ltd., Tokyo (JP)

(72) Inventors: Tadao Ohno, Ibaraki (JP); Mayu Yasunaga, Ibaraki (JP); Atsuo Ito, Ibaraki (JP); Yu Sogo, Ibaraki (JP); Fumiko Kobayashi, Ibaraki (JP)

(73) Assignees: Cell-Medicine, Inc., Ibaraki (JP); National Institute of Advanced Industrial Science and Technology, Tokyo (JP); University of Tsukuba, Ibaraki (JP); Nihon Parkerizing Co., Ltd., Tokyo (JP)

( * ) Notice: Subject to any disclaimer, the term of this patent is extended or adjusted under 35 U.S.C. 154(b) by 123 days.

(21) Appl. No.: 17/427,125

(22) PCT Filed: Jan. 30, 2020

(86) PCT No.: PCT/JP2020/003285
§ 371 (c)(1),
(2) Date: Nov. 4, 2021

(87) PCT Pub. No.: WO2020/158833
PCT Pub. Date: Aug. 6, 2020

(65) Prior Publication Data
US 2022/0193308 A1    Jun. 23, 2022

(30) Foreign Application Priority Data
Jan. 31, 2019 (JP) .................................. 2019-015509

(51) Int. Cl.
*A61L 27/42* (2006.01)
*A61L 27/54* (2006.01)

(52) U.S. Cl.
CPC ............. *A61L 27/425* (2013.01); *A61L 27/54* (2013.01); *A61L 2420/02* (2013.01); *A61L 2420/04* (2013.01)

(58) Field of Classification Search
CPC ..... A61L 27/425; A61L 9/00; A61B 17/7291; A61P 19/00
See application file for complete search history.

(56) References Cited

U.S. PATENT DOCUMENTS

| | | | |
|---|---|---|---|
| 5,100,688 A | 3/1992 | Cox et al. | |
| 5,730,933 A | 3/1998 | Peterson | |

(Continued)

FOREIGN PATENT DOCUMENTS

| | | |
|---|---|---|
| CN | 101143718 A | 3/2008 |
| CN | 101229366 A | 7/2008 |

(Continued)

OTHER PUBLICATIONS

Office Action in JP Application No. 202080025282.4 dated Aug. 15, 2022, (with corrected Examiner's Opinion), 14 pages.

(Continued)

*Primary Examiner* — Dah-Wei D. Yuan
*Assistant Examiner* — Andrew J Bowman
(74) *Attorney, Agent, or Firm* — MARSHALL, GERSTEIN & BORUN LLP

(57) ABSTRACT

A medical instrument in which an inorganic salt solid such as apatite into which a peptide hormone or the like is embedded is placed so that a metal or the like is coated therewith, in which the inorganic salt solid is provided by controlled delay co-precipitation or the like in an unstable supersaturated calcium phosphate solution, and the medical (Continued)

6 Claims, 11 Drawing Sheets

(56) References Cited

U.S. PATENT DOCUMENTS

| | | | |
|---|---|---|---|
| 5,783,217 A | 7/1998 | Lee et al. | |
| 6,136,369 A | 10/2000 | Leitao et al. | |
| 6,143,948 A | 11/2000 | Leitao et al. | |
| 6,207,218 B1 | 3/2001 | Layrolle et al. | |
| 6,344,061 B1 | 2/2002 | Leitao et al. | |
| 6,558,621 B1* | 5/2003 | Banks | A61L 2/20 |
| | | | 623/920 |
| 6,613,278 B1 | 9/2003 | Mills et al. | |
| 7,118,921 B1 | 10/2006 | Brennan et al. | |
| 2003/0080303 A1 | 5/2003 | Hayashi et al. | |
| 2003/0082232 A1 | 5/2003 | Lee et al. | |
| 2004/0153165 A1 | 8/2004 | Li et al. | |
| 2005/0065214 A1 | 3/2005 | Kronenthal | |
| 2008/0026032 A1* | 1/2008 | Zubery | A61P 19/00 |
| | | | 514/8.8 |
| 2008/0241353 A1 | 10/2008 | Liu | |
| 2008/0292779 A1* | 11/2008 | Mercuri | A61C 8/0012 |
| | | | 427/2.29 |
| 2008/0306554 A1 | 12/2008 | McKinley | |
| 2009/0166178 A1 | 7/2009 | Harmon et al. | |
| 2012/0093803 A1 | 4/2012 | Altrichter et al. | |
| 2013/0209508 A1 | 8/2013 | Daly et al. | |
| 2014/0030296 A1 | 1/2014 | Maruyama et al. | |
| 2015/0125511 A1 | 5/2015 | Kageyama et al. | |
| 2015/0132279 A1 | 5/2015 | Kageyama et al. | |
| 2018/0353598 A1 | 12/2018 | Ishii et al. | |
| 2019/0117780 A1 | 4/2019 | Jeffries et al. | |

FOREIGN PATENT DOCUMENTS

| | | | |
|---|---|---|---|
| CN | 101249278 A | 8/2008 | |
| CN | 101366954 B | 2/2009 | |
| CN | 102583286 A | 7/2012 | |
| CN | 103169658 A | 6/2013 | |
| CN | 104758981 A | 7/2015 | |
| CN | 107441549 A | 12/2017 | |
| EP | 562864 A1 | 9/1993 | |
| EP | 806212 A1 | 11/1997 | |
| EP | 562864 B1 | 12/2005 | |
| EP | 1786483 B1 | 11/2010 | |
| JP | H08-117323 A | 5/1996 | |
| JP | H09-133770 A | 5/1997 | |
| JP | H10-511957 A | 11/1998 | |
| JP | H11-506360 A | 6/1999 | |
| JP | 2000-93503 A | 4/2000 | |
| JP | 2002-501786 A | 1/2002 | |
| JP | 2002-529201 A | 9/2002 | |
| JP | 2003-503423 A | 1/2003 | |
| JP | 2003-320515 A | 11/2003 | |
| JP | 2003-321281 A | 11/2003 | |
| JP | 2005-112848 A | 4/2005 | |
| JP | 2005-132659 A | 5/2005 | |
| JP | 2007-513083 A | 5/2007 | |
| JP | 2007-515196 A | 6/2007 | |
| JP | 2008-074732 A | 4/2008 | |
| JP | 2008-231032 A | 10/2008 | |
| JP | 2009/018086 * | 1/2009 | A61L 27/00 |
| JP | 2009-018086 A | 1/2009 | |
| JP | 4478754 B2 | 6/2010 | |
| JP | 2010-167040 A | 8/2010 | |
| JP | 4569946 B2 | 10/2010 | |
| JP | 2011-229661 A | 11/2011 | |
| JP | 2012-521776 A | 9/2012 | |
| JP | 5221132 B2 | 6/2013 | |
| JP | 2015-109966 A | 6/2015 | |
| JP | 5746430 B2 | 7/2015 | |
| JP | 5872032 B2 | 3/2016 | |
| JP | 2016-53063 A | 4/2016 | |
| JP | 2016-106104 A | 6/2016 | |
| JP | 2016-173357 A | 9/2016 | |
| JP | 6082901 B2 | 2/2017 | |
| JP | 2017-222687 A | 12/2017 | |
| JP | 6317307 B2 | 4/2018 | |
| KR | 1998-0073699 A | 11/1998 | |
| WO | WO-96/20698 A2 | 7/1996 | |
| WO | WO-96/40297 A1 | 12/1996 | |
| WO | WO-99/38543 A2 | 8/1999 | |
| WO | WO-01/43143 A1 | 6/2001 | |
| WO | WO-2005/046746 A2 | 5/2005 | |
| WO | WO-2006/004778 A2 | 1/2006 | |
| WO | WO-2006/016807 A2 | 2/2006 | |
| WO | WO-2012/105224 A1 | 8/2012 | |
| WO | WO-2014/203204 A1 | 12/2014 | |
| WO | WO-2017/047095 A1 | 3/2017 | |

OTHER PUBLICATIONS

Extended European Search Report in EP Application No. 20749468.3 dated Feb. 14, 2022, 9 pages.

Office Action in CN Application No. 202080025282.4 dated Feb. 9, 2023, 9 pages.

Office Action in CN Application No. 202080025282.4 dated Aug. 15, 2022, (with corrected Examiner's Opinion), 14 pages.

Oyane et al., "Spontaneous Growth of a Laminin-apatite Nanocomposite in a Metastable Calcium Phosphate Solution", Biomaterials 27, 2006, pp. 167-175.

Kume, Tamikazu, Functional Size Analysis of Bioactive Materials by Radiation Inactivation, Radiation Chemistry, 57, 3, 1994, 17 pages.

"How the Manufacturing and Quality Control of Sterile Products are Implemented to lead to Social Contribution", PDA Journal of GMP and Validation in Japan, 16, pp. 9-14, 2014, 10 pages.

European Medicines Agency, Guideline on the sterilization of the medicinal product, active substance, excipient and primary container_ Draft, Apr. 11, 2016, 15 pages.

"Guidance for Manufacturing of Aseptic Drug Product by Terminal Sterilization Method", Health and Labour Science Research, 2011, 59 pages.

Biological Mechanisms of Radiation Protection, Shikita Mikio, Radioisotopes, 24, pp. 894-901, 1975, 10 pages.

Recent Trend in the Study of Radioprotective Substances, Shikita Mikio, Journal of Atomic Energy Society of Japan, 35, pp. 688-693, 1993, 16 pages.

The Research on Radioprotector and Radiosensitizer Using C3H Mice, Hasegawa et al., Research reports of Suzuka University of Medical Science, 9, pp. 87-96, 2002, 22 pages.

Establishment of a Novel Screening Method Which Accelerates Development of Radioprotective Agents, Sekine (Suzuki) Emiko, Isotope News, 710, pp. 2-6, 2013, 12 pages.

Chemical Screening of Radiation Protecting Agents, Yamamoto et al., Radioisotopes, 30, pp. 258-262, 1981, 6 pages.

Radioprotection by Metals: Selenium, J.F. Weiss et al., Adv. Space Res., 12, pp. 223-231, 1992.

Sodium Orthovanadate Inhibits p53-Mediated Apoptosis, Morita et al., Cancer Res., 70, pp. 257-265, 2010.

The Effect of Zinc Sulphate in the Prevention of Radiation-induced Dermatitis, Ertekin MV, et al., J. Radiat. Res., 45, pp. 543-548, 2004.

EMA Non-compliance Report (Vaccines)—20 DICM/INSP/AMG/MBP/ACS, GMP Information Digest, Virtual Pharmaceutical Plant, Jan. 8, 2017, http://ncogmp.com/blog/emanoncompliancereport-vaccine-dicminspamgmbpacs/, 5 pages.

Yamaguchi Toru, "New Trend of Sterilization of Drug products and Medical Instruments", "Radiation sterilization" [Third Session], Sep. 17, 2015 https://www.gmp-platform.com/article_detail.html?id=611, 10 pages.

"Influence of Gamma-Ray Irradiation on Substances for Drug Products"—Radiation Use Technology Database (RADA), 1996, 8 pages.

(56) References Cited

OTHER PUBLICATIONS

Alternations of Guidance for Manufacturing of Aseptic Drug Product by Terminal Sterilization Method, Notices from Ministry of Health, Labour and Welfare, Nov. 9, 2012, 61 pages.

Effect of Hydroxyapatite Formation on Titanium Surface With Bone Morphogenetic Protein-2 Loading Through Electrochemical Deposition on MG-63 Cells, Huei Yu Huang et al., Materials, 11, 1897, 2018, 11 pages.

Essential Requirement of Hepapin/FGF Receptor Complex for FGF Binding to Their Receptors: Regulation of FGF Function by Extracellular Matrix, Mikio Kan et al., Tiss. Cul. Res. Commun., 1992, vol. 11, pp. 345-352.

Enhanced Bone Formation Using Hydroxyapatite Ceramic Coated With Fibroblast Growth Factor-2, Tsurushima, H. et al., Acta Biomaterialia, 2010, vol. 6, pp. 2751-2759.

Fibroblast Growth Factor-2-Apatite Composite Layers on Titanium Screws to Reduce Pin Tract Infection Rate, Mutsuzaki, H. et al., J. Biomed. Mater. Res. Part B: Appl. Biomater., 2008, vol. 86B, pp. 365-374.

Initial Clinical Trial of Pins Coated With Fibroblast Growth Factor-2-apatite Composite Layer in External Fixation of Distal Radius Fractures, Yanagisawa, Y. et al., Journal of Orthopaedics, 2018, vol. 16, pp. 69-73.

Search Report in International Application No. PCT/JP2020/003285 dated Apr. 14, 2020, 3 pages.

Office Action in CN Application No. 202080025282.4 dated Jun. 6, 2023, 8 pages.

Decision of Refusal in CN Application No. 202080025282.4 dated Sep. 8, 2023, 12 pages.

Bae et al., "Heparin is a Highly Charged New Functional Polymer", J. Korean Ind. Eng. Chem., vol. 15, No. 7, Nov. 2004, pp. 693-701.

Office Action in KR Application No. 10-2021-7027406 dated Jan. 30, 2024, 5 pages.

* cited by examiner

US 12,178,939 B2

INORGANIC SALT-PROTEIN COMPOSITE MEDICAL INSTRUMENT

TECHNICAL FIELD

The present invention relates to an ionizing radiation sterilization-resistant medical instrument including a crystal of an inorganic salt or an amorphous solid of an inorganic salt (hereinafter, herein sometimes simply referred to as "inorganic salt solid"), and a protein having bioactivity.

More particularly, the present invention relates to a medical instrument for use in mammals including human being, wherein the medical instrument includes an inorganic salt solid into which a protein having bioactivity, not to be recognized as any foreign substance by the mammals, is embedded, and the medical instrument is sterilized by ionizing radiation with bioactivity of the protein being kept, by means of ionizing radiation sterilization resistance attained by embedding.

BACKGROUND ART

Embedding is a term for use in pathology. The term refers to fixation of living tissues serving as subjects for pathological examinations, by implanting and solidifying of the living tissues in liquid paraffin or resin which can be solidified. In pathological examinations, tissue-embedded blocks are sliced by microtome or the like to thereby provide sections (prepared slides) for histological stain and such sections are subjected to microscopic examinations or the like. In the present description, such a concept is expanded, and implanting the entire protein molecule or a part thereof into an inorganic salt solid, or densely surrounding the entire protein molecule or a part thereof and fixing such a protein molecule into an inorganic salt solid is called "embedding". The state of "embedding" is different from the state of simple "adsorption" or "contact" of the protein molecule to or with the inorganic salt solid, or the state of "mixing" of the protein molecule and the inorganic salt solid.

Actual examples of "embedding" of a protein molecule in an inorganic salt solid may include a composition obtained by co-precipitating a protein molecule and calcium phosphate from a supersaturated calcium phosphate solution with which a protein coexist, and dispersing and disposing the protein molecule in a calcium phosphate matrix at an interval in the order of nanometers (Non-Patent Document 1).

Products and raw materials, such as drug products and medical instruments, for use in the medical field where sterility is required, are sterilized by various methods in production processes. Among sterilization methods, a sterilization method utilizing characteristics of radiation which easily passes through substances corresponds to ionizing radiation sterilization. Such ionizing radiation sterilization is easily applied particularly in a terminal step of production and thus is widely used as a terminal sterilization method in a case where modification and deactivation of objects by ionizing radiation irradiation do not matter.

While the type and the dose of ionizing radiation used are varied depending on the type, the number, and the presence form of bacteria which are expected to be present in objects to be sterilized, gamma rays, which have high permeability, are often used for medical tools, and an appropriate dose thereof for sterilization is representatively 25 kGy and a dose around this dose is widely used. When surfaces of objects are to be sterilized, electron beams are also widely used because of their high dose rate and short irradiation time.

However, any sterilization method easily causes deactivation of substances having bioactivity. In particular, nucleic acids and proteins are large in molecular sizes and thus are easily deactivated in ionizing radiation sterilization, and, that is shown by the fact that a radiation deactivation method is established as a method of measuring the molecular weight of an active domain of protein in vivo (Non-Patent Document 2). The concept "biological formulations are products which are very difficult to aseptically control in production by application of an aseptic production process because no terminal sterilization method can be applied" (Non-Patent Document 3) is commonly taken for granted, and the published Draft of Guideline on the sterilization of the medicinal product in European Medicines Agency (Non-Patent Document 4) also describes "For highly sensitive products such as biological products where terminal sterilization of the drug product is not possible, aseptic processing under controlled conditions provides a satisfactory quality of the drug product". "Guidance for Manufacturing of Aseptic Drug Product by Terminal Sterilization Method" (Non-Patent Document 5) is disclosed. However, there is no mention about any method of protecting the activity of a drug product to be sterilized.

Ionizing radiation non-specifically hits various compounds to make radicals, regardless of the type thereof. Transition of radical electrons may occur on radical generation sites to lead to the occurrence of a radical reaction of any compound completely different from the original compound. If such a radical reaction causes unnatural changes in compounds important for DNA, membrane lipids and cells, cells will be harmed (Non-Patent Document 6). Such harmful action, if exerted on bacteria and viruses, would be sterilization. Similarly, a protein having bioactivity, if reacted with any radical, would be deactivated.

Thiols like cysteine and glutathione are known as radioprotective agents for deactivating harmful radicals, and representative examples thereof include aminothiol derivatives. Cysteamine (mercaptoethylamine), WR-2721 (S-2-(3-Aminopropylamino) ethylphosphorothioic acid), and the like have been known for a long time (Non-Patent Document 7). Additionally, 2-mercaptoethylamine and alcohol (ethanol) are also described in Document (Non-Patent Document 8). Moreover, (+)catechin, curcumin, vitamin C, resveratrol, caffeine acid, and quercetin are described as substances exerting radioprotective effects in screening where cytotoxicity is evalutated as an index (Non-Patent Document 9). Furthermore, nitrogen-containing compounds are described as substances exerting radioprotective effects (Non-Patent Document 10). Additionally, amino acid mixtures are also known to have radioprotective effect on bioactive proteins (Patent Documents 1 and 2). Furthermore, as methods of suppressing deactivation of proteins in sterilization by ionizing radiation, a method of suppression by coexistence with a cellulose ether derivative and/or a specific group of amino acids (Patent Documents 3 and 4), a method of suppression by coexistence with an aliphatic polyester (Patent Document 5), and a method of suppression by coexistence with an exogenous protein such as gelatin (Patent Document 6) are disclosed. However, all the foregoings are radioprotective agents of organic substances. While a method involving coexistence of a bioactive protein with collagen sponge and/or an absorbable polymer is disclosed (Patent Documents 7 and 8), a method for suppressing deactivation in sterilization by ionizing radiation is not disclosed.

On the other hand, there are known radioprotective agents of inorganic substances, for example, selenium (Non-Patent Document 11), vanadate (Non-Patent Document 12), zinc sulfate (Non-Patent Document 13), and manganese compounds (Patent Documents 9 and 10). However, many inorganic salts, when adopted in medical instruments for mammals, are feared to have toxicity, and therefore are not subjects to be developed as radioprotective agents for medical use.

Among inorganic substances, calcium phosphate has high safety and biocompatibility, and, for example, respective crystals of apatite (Ca/P molar ratio 1.67) and tricalcium phosphate (Ca/P molar ratio 1.50) which are different in molar ratio of Ca ion to $PO_4$ ion, and amorphous calcium phosphate (Ca/P molar ratio 1 to 1.8) are used for medical instruments and the like.

A method of measuring a dose by using fired apatite, according to electron spin resonance analysis of radical generated in irradiation of calcium phosphate with ionizing radiation (Patent Document 11). However, the dose range described is about 0 to 60 Gy, and there is no mention of irradiation in a dose range suited for ionizing radiation sterilization (several kGy or more, usually often 10 to 30 kGy) which is more than 1000 times higher than that, or radioprotective effect on other bioactive molecules coexisting.

Japanese Translation of PCT International Application Publication No. H11-506360 (Patent Document 12) is known as a document which mentions the protective effect on a bioactive protein in the case of irradiation of apatite or hydroxyapatite as an inorganic salt at any irradiance suitable for sterilization. This document mentions that "any one or a combination of materials including ceramics (for example, hydroxyapatite, tricalcium phosphate, or a combination thereof with any other calcium phosphate (without limitation), can be advantageously used" as one insoluble synthetic polymer carrier material containing a bioactive osteogenic protein, and describes a terminally sterilized osteogenic device for transplantation into mammals.

However, this document does not refer which modes of "any one or a combination" of a bioactive osteogenic protein and materials including ceramics are to be adopted, at all. Examples of the type of the combination mode of the bioactive osteogenic protein and the material include "mixing", "adsorption", "contact", and "embedding" (hereinafter, collectively referred to as "type of combination mode"), and not only the document does not mention a large difference in bioactivity of the protein after terminal sterilization due to the difference in type of combination mode, but also it neither describes nor indicates which combination mode is an optimal combination mode in which terminal sterilization can be perfomed with bioactivity of the osteogenic protein being maintained.

Japanese Translation of PCT International Application Publication No. 2007-513083 (Patent Document 13) discloses a sterilizable composition which is a medical graft and which includes an inorganic salt and a bioactive protein. However, this document also neither describes nor indicates that a large difference in bioactivity of a protein after terminal sterilization is caused due to the difference in type of combination mode of an inorganic salt and a bioactive protein, and which combination mode can be adopted as an optimal combination mode in which terminal sterilization can be performed with bioactivity of the bioactive protein being maintained.

Japanese Translation of PCT International Application Publication No. 2007-515196 (Patent Document 14) discloses a composition as a putty for control of bone bleeding, the composition including hydroxyapatite as an inorganic salt, and a bone growth inducing substance, but mentions that terminal sterilization cannot be performed in a case where the bone growth inducing substance is a radiosensitive bioactive protein such as a demineralized bone matrix or a bone morphogenetic protein.

Japanese Translation of PCT International Application Publication No. 2002-501786 (Patent Document 15) discloses a bone paste composition including gelatin sterilized by heating or radiation, an osteogenic component such as a regenerative/proliferative factor, and an inorganic salt such as calcium phosphate ceramic, but neither describes nor indicates that the composition is formed and then finally sterilized by radiation irradiation and heat treatment.

Japanese Translation of PCT International Application Publication No. 2002-529201 (Patent Document 16) discloses a graft to be transplanted into human, the graft including ceramics as an inorganic salt, a bioactive substance as a proliferative factor, and furthermore a allogeneic, autologous or xenogeneic graft tissue, but terminal sterilization is performed by "irradiation with γ-ray or another type of ray at a dose which is well-known not to have any harmful influence on tissue characteristics", or by electron beam sterilization or ethylene oxide sterilization "as long as it causes neither any toxicity nor deterioration in desired bioactivity". In other words, it is considered that sacrifice of the sterilization effect of radiation is accepted in order to allow bioactivity to be maintained, and a harmful influence and deterioration in bioactivity are prevented by limiting the dose of irradiation. A solution here only described is "to inject a desirable bioactive substance to the graft, as a further enhancement", if necessary, before terminal sterilization.

Japanese Translation of PCT International Application Publication No. H10-511957 (Patent Document 17) discloses a radiation-sterilized nanoparticle having an average size of less than 300 nm and including a core made of a biocompatible-biodegradable polymer, in which the nanoparticle contains a bioactive agent and is combined with apatite and/or bone ceramics, but gives no mention about any method of preventing deactivation of the bioactive agent by radiation sterilization and gives no mention which combination mode can be adopted as an optimal combination mode in which terminal sterilization can be performed with activity being maintained.

Japanese Translation of PCT International Application Publication No. 2003-503423 (Patent Document 18) describes a carrier to be sterilized after synthesis, in which bioactivity is incorporated into a carrier matrix including an inorganic, organic, or organic and inorganic substance, but neither describes nor indicates which type of combination mode of the carrier matrix including an inorganic, organic, or organic and inorganic substance allows bioactivity to be maintained also after sterilization, or which sterilization method allows bioactivity to be maintained also after sterilization.

Japanese Patent No. 5221132 (Patent Document 19) describes a method of obtaining a substrate coated, by contacting a substrate with an acidified composition including a brine mixture including calcium, magnesium, phosphoric acid, hydrogen carbonate ion and a bioactive substance, to result in an increase in pH to thereby allow for co-precipitation of a salt and the bioactive substance. Although there is no mention in the invention recited in claims, the detailed description describes gamma-ray irradiation which can also be performed after the last step (paragraph [0020] describes "the method can also be performed with gamma-ray irradiation at the last stage following step c), in a condition of no aseptic and sterile state"). However, such gamma-ray irradiation is here merely mentioned as one example of a common sterilization procedure which can be taken, and there is not disclosed any specific experimental example for performing sterilization by such gamma-ray irradiation. Moreover, the substrate is here any of substrates made of different materials such as a metal, ceramic, and a polymer, and there is neither described nor indicated whether bioactivity is maintained after gamma-ray irradiation in respective cases of all such substrates made of these materials or bioactivity is maintained after gamma-ray irradiation in only a case of such a substance made of a specific material, or which mode is adopted to allow bioactivity to be maintained also after gamma-ray irradiation.

International Publication No. WO 2006/004778 (Patent Document 33) describes an implant having a coating layer in which a peptide having a cell adhesion promotion effect is incorporated in a nanocrystalline apatite layer, and Examples therein describe no deterioration in cell adhesion promotion effect after irradiation with γ-rays at 25 kgrey in an implant where hydroxyapatite is electrochemically sedimented in a disc made of titanium in the presence of peptide to incorporate an apatite layer into the peptide, and, on the other hand, loss in cell adhesion promotion effect after irradiation with γ-rays in an implant where peptide merely adsorbs onto the surface of an apatite layer (Examples 1 and 2).

However, the implant disclosed in the above Patent Document is obtained by electrochemical sedimentation of hydroxyapatite, and is not a composite produced by co-precipitation with peptide in a supersaturated calcium phosphate solution. One obtained by incorporating peptide into an apatite layer by electrochemical sedimentation and a composite obtained by co-precipitation of peptide with apatite are fully different in microscopic structure and crystallinity.

In other words, apatite formed by electrochemical sedimentation has high crystallinity to such an extent that (002) (211) (112) (300) diffraction lines are separated in a powder X-ray diffraction method (for example, Non-Patent Document 18), and easily takes, as a crystal form, a hexagonal needle-like or hexagonal plate-like form characteristic of an apatite crystal. Apatite has high crystallinity and thus has low solubility (Patent Document 33). Apatite with low solubility is suitable for providing a composite of a peptide or protein which is not required to be gradually released and for which it is only important to be fixed on a surface. One example of such a peptide or protein which is not required to be gradually released and for which it is only important to be fixed on a surface is a peptide or protein having a cell adhesion promotion effect. In fact, this Patent Document also mentions that needle-like apatite is formed, the apatite is low in solubility and stable, and a peptide having a cell adhesion promotion effect is stably and strongly bound to a surface. In this regard, a peptide or protein having cell proliferation activity, tissue formation activity, cell differentiation promotion activity, reaction activity with an antibody, agonistic action activity, and antagonistic action activity is gradually released and thus exerts the effect on surrounding tissues, and thus incorporation thereof into apatite with high crystallinity and low solubility is not suitable. It is rather necessary to appropriately reduce the solubility of apatite or calcium phosphate to thereby allow a peptide or protein incorporated to be gradually released.

Coatings by electrochemical sedimentation originally can be applied to conductive metals, but cannot be applied to non-conductive ceramics. This Patent Document does not disclose any example where polysaccharide (for example heparin) which is derived from an extracellular matrix and which, by itself, does not have direct cell proliferation/differentiation activity is allowed to coexist with peptide and the peptide is thus incorporated into a layer of hydroxyapatite.

Immunoadjuvants of inorganic salts may be sometimes used together with antigens in vaccination aiming induction of the body's immune reaction. Immunoadjuvants of inorganic salts, widely used for a long period, are aluminum salts such as aluminum chloride, aluminum phosphate, and aluminum sulfate, in addition to aluminum hydroxide, and calcium phosphate is also used. Calcium phosphate immunoadjuvants include a vaccine adjuvant designated as a cancer-specific antigen vaccine, which is obtained by combining a cancer-specific antigen derived from an organism with 3-tricalcium phosphate as an inorganic salt (Patent Documents 20 and 21), and a calcium phosphate immunoadjuvant to be used with an antigen (Patent Documents 22 and 23), but all the Patent Documents do not mention any radiation sterilization after combining with the antigen which is a protein. Aluminum salt immunoadjuvants have a long history of being combined with antigens such as bacteria or viruses and used as vaccines for preventing infection, and among them, and some of such vaccines are produced through terminal sterilization by radiation (Non-Patent Document 14).

However, such antigens such as bacteria or viruses are biomolecules of organisms different from animals as subjects of vaccine administration, or xenogeneic organisms, and are proteins recognized as exogenous by such animals to be administrated or transplanted. Therefore, these Documents do not disclose radiation sterilization of a protein not recognized as exogenous by such animals to be administrated or transplanted. Antigens such as bacteria or viruses are originally exogenous for animals to be administrated and thus eliminated by the immune system. Thus, such antigens, even if unnaturally changed in their molecules by radiation sterilization, are still exogenous, and are accordingly considered to have a relatively small adverse influence on the intended effect (elimination by the immune system). In this regard, when an effect such as tissue regeneration is obtained by using a protein not recognized to be exogenous by animals to be administrated or transplanted, an unnatural change in molecule due to radiation sterilization has an adverse influence on functions of the protein, for example, recognized to be exogenous and no occurrence of binding with any receptor, and the intended effect is considered to be hardly obtained.

In view of such circumstances, known examples of a bioactive protein which is, in particular, not a short chain peptide having up to about 50 amino acid residues, but a long chain protein having even 50 or more amino acid residues, and corresponds to a biological formulation to which a terminal sterilization method with radiation is applied, include only chymotrypsin and papain (Non-Patent Documents 15 and 16).

RELATED ART DOCUMENTS

Patent Documents

Patent Document 1: International Publication No. WO 01/043143
Patent Document 2: Japanese Patent Application Publication No. 2016-53063
Patent Document 3: Japanese Patent No. 5872032
Patent Document 4: Japanese Patent No. 6317307
Patent Document 5: Japanese Patent No. 5746430
Patent Document 6: U.S. Pat. No. 5,730,933
Patent Document 7: EP Patent No. 0562864 A1
Patent Document 8: EP Patent No. 0562864 B1
Patent Document 9: Japanese Patent Application Publication No. 2016-106104
Patent Document 10: Japanese Patent Application Publication No. 2017-222687
Patent Document 11: Japanese Patent Application Publication No. H09-133770
Patent Document 12: Japanese Translation of PCT International Application Publication No. H11-506360
Patent Document 13: Japanese Translation of PCT International Application Publication No. 2007-513083
Patent Document 14: Japanese Translation of PCT International Application Publication No. 2007-515196
Patent Document 15: Japanese Translation of PCT International Application Publication No. 2002-501786
Patent Document 16: Japanese Translation of PCT International Application Publication No. 2002-529201
Patent Document 17: Japanese Translation of PCT International Application Publication No. H10-511957
Patent Document 18: Japanese Translation of PCT International Application Publication No. 2003-503423
Patent Document 19: Japanese Patent No. 5221132
Patent Document 20: Japanese Patent No. 6082901
Patent Document 21: International Publication No. WO 2012/105224
Patent Document 22: International Publication No. WO 2017/047095
Patent Document 23: Japanese Patent No. 4569946
Patent Document 24: Japanese Patent Application No. 2016-173357
Patent Document 25: EP Patent No. 806212
Patent Document 26: Japanese Patent Application Publication No. 2000-93503
Patent Document 27: EP Patent No. 1786483 B1 (EP Patent corresponding to Patent Document 17)
Patent Document 28: International Publication No. WO 2006/016807
Patent Document 29: Japanese Patent No. 4478754
Patent Document 30: U.S. Pat. No. 6,136,369
Patent Document 31: U.S. Pat. No. 6,143,948
Patent Document 32: U.S. Pat. No. 6,344,061
Patent Document 33: International Publication No. WO 2006/004778

Non-Patent Documents

Non-Patent Document 1: Biomaterials, 27, pp. 167-175, 2006
Non-Patent Document 2: Radiation Chemistry, 57, 3, 1994
Non-Patent Document 3: GMP Committee to Sterile Products in PDA Japan, "How the Manufacturing and Quality Control of Sterile Products are Implemented to Lead to Social Contribution", PDA Journal of GMP and Validation in Japan, 16, pp. 9-14, 2014
Non-Patent Document 4: European Medicines Agency, Guideline on the sterilization of the medicinal product, active substance, excipient and primary container_Draft, Apr. 11, 2016
Non-Patent Document 5: "Guidance for Manufacturing of Aseptic Drug Product by Terminal Sterilization Method", Health and Labour Science Research, 2011, (Total Research Business of Pharmaceutical and Medical Device Regulatory Science), Announcements from Pharmaceutical and Food Safety Bureau Compliance and Narcotics Division of Ministry of Health, Labour and Welfare, 2011
Non-Patent Document 6: RADIOISOTOPES, 24, pp. 894-901, 1975
Non-Patent Document 7: Journal of Atomic Energy Society of Japan, 35, pp. 688-693, 1993
Non-Patent Document 8: Research reports of Suzuka University of Medical Science, 9, pp. 87-96, 2002
Non-Patent Document 9: Isotope News, 710, pp. 2-6, 2013
Non-Patent Document 10: RADIOISOTOPES, 30, pp. 258-262, 1981
Non-Patent Document 11: Adv. Space Res., 12, pp. 223-231, 1992
Non-Patent Document 12: Cancer Res., 70, pp. 257-265, 2010
Non-Patent Document 13: Ertekin M V, et al., J. Radiat. Res., 45, pp. 543-548, 2004
Non-Patent Document 14: EMA Non-compliance Report (Vaccines)—DICM/INSP/AMG/MBP/ACS, GMP Information Digest, Virtual Pharmaceutical Plant, 2017.1.8, http://ncogmp.com/blog/emanoncompliancereport-vaccine-dicminspamgmbpacs/
Non-Patent Document 15: "New Trend of Sterilization of Drug products and Medical Instruments", "Radiation sterilization" [Third Session], 2015.09.17 http://www.gmp-platform.com/topics_detail1/id=1010
Non-Patent Document 16: "Influence of Gamma-Ray Irradiation on Substances for Drug Products"—Radiation Use Technology Database (RADA), 1996
Non-Patent Document 17: "Alternations of Guidance for Manufacturing of Aseptic Drug Product by Terminal Sterilization Method", Notices from Ministry of Health, Labour and Welfare, Nov. 9, 2012
Non-Patent Document 18: Materials, 11, 1897, 2018

SUMMARY OF THE INVENTION

Problems to be Solved by the Invention

An object of the present invention is to provide a medical instrument for use in animals, including a bioactive protein which retains bioactivity even after radiation-sterilized.

Another object of the present invention is to provide a method of producing a medical instrument for use in mammals, in which the medical instrument includes a bioactive protein which retains bioactivity even after radiation-sterilized.

Still another object of the present invention is to provide a medical instrument for use in mammals, a medical instrument for bone tissue repair, an artificial joint or the like, including a bioactive protein which retains bioactivity even if radiation-sterilized.

Still another object of the present invention is to provide a method of producing a medical instrument for use in mammals, for example, a medical instrument for bone tissue repair or an artificial joint, in which the medical instrument or the artificial joint includes a bioactive protein which retains bioactivity even after radiation-sterilized.

Means for Solving the Problems

The present inventors have made intensive studies in order to solve the above problems, and as a result, have found that a composite where an inorganic salt and a bioactive protein are co-precipitated is formed in embedding of the bioactive protein into an inorganic salt solid, to thereby allow deactivation of the protein to be considerably suppressed even in irradiation at a dose suitable for sterilization. In other words, it has been found that the inorganic salt solid by itself has useful radioprotective effect.

For example, calcium phosphate can easily form a supersaturated solution depending on conditions. Any (physical or chemical) stimulation immediately disrupt the supersaturated state, and calcium phosphate is deposited to generate a precipitate. If a bioactive protein is here added as a solute into the supersaturated solution, calcium phosphate will be precipitated with entangling the protein, and will produce a composition where calcium phosphate such as apatite is co-precipitated and deposited with the protein being embedded. In a composition obtained by freeze-drying the precipitate, deactivation of the bioactive protein was considerably suppressed even after gamma-ray irradiation at a dose suitable for sterilization. In a composition obtained by embedding the bioactive protein into sodium chloride and vacuum-drying the resultant, deactivation of the bioactive protein due to gamma-ray irradiation at a dose suitable for sterilization was considerably suppressed similarly. These findings indicate that deactivation of the bioactive protein can be prevented by suppressing generation of radical in irradiation, and the present invention has been completed based on the findings.

Specifically, the present invention encompasses the followings.

[1] A medical instrument for use in mammals including human being, in which an inorganic salt solid into which a protein having bioactivity is embedded is placed so that a metal, a ceramic or both thereof is partially or entirely coated with the inorganic salt solid, wherein
  (a) the inorganic salt solid into which a protein having bioactivity is embedded is provided in a step of controlled delay co-precipitation in a neutral or weak alkaline unstable supersaturated calcium phosphate solution which generates spontaneous nucleation, a coverage sandwich method or a drying method,
  (b) the medical instrument is produced in a step of producing a terminally sterilized medical instrument having one or more bioactivities selected from the group consisting of cell proliferation activity, vascular proliferation activity, soft tissue formation activity, bone tissue formation activity, bone differentiation promotion activity, reaction activity with an antibody, agonistic action activity, and antagonistic action activity, by exposure to ionizing radiation at a dose sufficient for sterilization,
  (c) the inorganic salt is one or more inorganic salts selected from the group consisting of apatite, tricalcium phosphate, octacalcium phosphate, amorphous calcium phosphate, and calcium carbonate, and
  (d) the protein having bioactivity is one or more proteins selected from the group consisting of a peptide hormone, a growth factor, and an osteogenic protein.

[2] The medical instrument according to [1], wherein the apatite is low crystalline apatite.

[3] The medical instrument according to [1] or [2], wherein the delay co-precipitation comprises artificial control delay for a time taken until calcium phosphate deposition by controling a KCl concentration in an aqueous solution comprising 0.5 to 2.5 mM of Ca ion, 1.0 to 20 mM of phosphate ion, 0 to 40 mM of K ion, 0 to 200 mM of Na ion, and 0 to 200 mM of Cl ion, and having a pH of 7.0 to 9.0, as the unstable supersaturated calcium phosphate solution.

[4] The medical instrument according to [1] or [2], wherein the delay co-precipitation comprises artificial control delay for a time taken until calcium phosphate deposition by controling a KCl concentration in an aqueous solution comprising 1.2 to 2.75 mM of Ca ion, 0.6 to 15 mM of phosphate ion, 0 to 30 mM of K ion, 30 to 150 mM of Na ion, 0.1 to 3.0 mM of Mg ion, 30 to 150 mM of Cl ion, and 0 to 60 mM of $HCO_3$ ion, and having a pH of 7.0 to 9.0, as the unstable supersaturated calcium phosphate solution.

[5] The medical instrument according to any of [1] to [4], wherein polysaccharide which is derived from an extracellular matrix and which has, by itself, no direct cell proliferation/differentiation activity, preferably heparin, is further embedded into the inorganic salt solid into which the protein having bioactivity is embedded.

[6] The medical instrument according to any of [1] to [5], wherein the metal is one or more metals selected from the group consisting of titanium, a titanium alloy, stainless steel, and a cobalt/chromium alloy.

[7] The medical instrument according to any of [1] to [5], wherein the ceramic is one or more ceramics selected from the group consisting of apatite, tricalcium phosphate, octacalcium phosphate, amorphous calcium phosphate, alumina, zirconia, and a composite thereof.

[8] The medical instrument according to any of [1] to [7], wherein the ionizing radiation is a gamma ray and/or an electron beam.

[9] The medical instrument according to [8], wherein the sterilization by the gamma ray and/or the electron beam is performed under a condition where generation of radical is suppressed, and the condition is one or more conditions selected from the group consisting of (a) sterilization in a degassing state at an atmospheric pressure of 50 kPa, (b) sterilization in a state where air is replaced with a nitrogen or inert gas, (c) sterilization at a low temperature ranging from 0° C. to −196° C., and (d) sterilization in a state where ascorbic acid or ascorbate is further added to the inorganic salt solid into which the protein having bioactivity is embedded.

[10] The medical instrument according to [9], wherein the ascorbic acid or ascorbate is selected from the group consisting of ascorbic acid, sodium ascorbate, calcium ascorbate dihydrate, and ascorbic acid phosphate magnesium salt n-hydrate.

[11] The medical instrument according to any of [8] to [10], wherein the dose of the gamma ray is 3 to 40 kGy.

[12] The medical instrument according to any of [1] to [11], wherein the peptide hormone is one or more peptide hormones selected from the group consisting of a hypothalamus-derived peptide hormone, vasopressin, oxytocin, intermedin, a gonadotrophic hormone, a growth hormone, a parathyroid hormone, inhibin, activin, relaxin, insulin, glucagon, somatostatin, cholecystokinin, secretin, motilin, atrial natriuretic peptide, erythropoietin, leptin, endothelin, ghrelin, adiponectin, an insulin-like growth factor, and calcitonin gene-related peptide.

[13] The medical instrument according to any of [1] to [11], wherein the growth factor is one or more growth factors selected from the group consisting of FGF-2 and a functional equivalent thereof.

[14] The medical instrument according to any of [1] to [11], wherein the osteogenic protein is one or more osteogenic proteins selected from the group consisting of OP-1, OP-2, BMP-2, BMP-3, BMP-4, BMP-5, BMP-6, BMP-8, BMP-9, DPP, Vg1, Vgr-1, and functional equivalents thereof.

[15] The medical instrument according to any of [1] to [14], wherein the bioactivity after terminal sterilization by the ionizing radiation at a dose sufficient for sterilization is 13% or more relative to the bioactivity before the sterilization.

[16] The medical instrument according to any of [1] to [15], for use in tissue repair.

[17] The medical instrument according to [16], wherein the medical instrument is one or more medical instruments selected from the group consisting of an intracorporeal fixation pin, an intracorporeal fixation screw, an artificial bone, a bone prosthetic material, a dental endosseous implant, a spinal fixation device, an intramedullary nail, and a spinal cage.

[18] The medical instrument according to any of [1] to [15], for use as an artificial joint.

[19] A method of producing a medical instrument for use in mammals including human being, in which an inorganic salt solid into which a protein having bioactivity is embedded is placed so that a metal, a ceramic or both thereof is partially or entirely coated with the inorganic salt solid, wherein the method includes:

(a) a step of producing the inorganic salt solid into which the protein having bioactivity is embedded, by controlled delay co-precipitation in a neutral or weak alkaline unstable supersaturated calcium phosphate solution which generates spontaneous nucleation, a coverage sandwich method or a drying method, and (b) a step of producing the medical instrument as a terminally sterilized medical instrument having one or more bioactivities selected from the group consisting of cell proliferation activity, vascular proliferation activity, soft tissue formation activity, bone tissue formation activity, bone differentiation promotion activity, reaction activity with an antibody, agonistic action activity, and antagonistic action activity, by exposure to ionizing radiation at a dose sufficient for sterilization.

[20] A method of producing a medical instrument for use in mammals including human being, in which an inorganic salt solid into which a protein having bioactivity is embedded is placed so that a metal, a ceramic or both thereof is partially or entirely coated with the inorganic salt solid, wherein the method includes:

(a) a step of producing the inorganic salt solid into which the protein having bioactivity is embedded, by controlled delay co-precipitation in neutral or weak alkaline unstable supersaturated calcium phosphate solution which generates spontaneous nucleation, a coverage sandwich method or a drying method, and (b) a step of producing the medical instrument as a terminally sterilized medical instrument having one or more bioactivities selected from the group consisting of cell proliferation activity, vascular proliferation activity, soft tissue formation activity, bone tissue formation activity, bone differentiation promotion activity, reaction activity with an antibody, agonistic action activity, and antagonistic action activity, by exposure to ionizing radiation at a dose sufficient for sterilization, in which the bioactivity of the terminally sterilized medical instrument is at least about 13% or more relative to that before sterilization.

[21] The method according to [19] or [20], wherein the inorganic salt is one or more inorganic salts selected from the group consisting of low crystalline apatite, tricalcium phosphate, octacalcium phosphate, amorphous calcium phosphate, and calcium carbonate.

[22] The method according to any of [19] to [21], wherein the delay co-precipitation comprises artificial control delay for a time taken until calcium phosphate deposition by controlling a KCl concentration in an aqueous solution comprising 0.5 to 2.5 mM of Ca ion, 1.0 to 20 mM of phosphate ion, 0 to 40 mM of K ion, 0 to 200 mM of Na ion, and 0 to 200 mM of Cl ion, and having a pH of 7.0 to 9.0, as the unstable supersaturated calcium phosphate solution.

[23] The method according to any of [19] to [21], wherein the delay co-precipitation comprises artificial control delay for a time taken until calcium phosphate deposition by controlling a KCl concentration in an aqueous solution comprising 1.2 to 2.75 mM of Ca ion, 0.6 to 15 mM of phosphate ion, 0 to 30 mM of K ion, 30 to 150 mM of Na ion, 0.1 to 3.0 mM of Mg ion, 30 to 150 mM of Cl ion, and 0 to 60 mM of $HCO_3$ ion, and having a pH of 7.0 to 9.0, as the unstable supersaturated calcium phosphate solution.

[24] The method according to any of [19] to [23], wherein the step of producing the inorganic salt solid into which the protein having bioactivity is embedded comprises a step of producing an inorganic salt solid in which not only a protein having bioactivity, but also polysaccharide which is derived from an extracellular matrix and which has, by itself, no direct cell proliferation/differentiation activity, preferably heparin, is embedded.

[25] The method according to any of [19] to [24], wherein the metal is one or more metals selected from the group consisting of titanium, a titanium alloy, stainless steel, and a cobalt/chromium alloy.

[26] The method according to any of [19] to [24], wherein the ceramic is one or more ceramics selected from the group consisting of apatite, tricalcium phosphate, octacalcium phosphate, amorphous calcium phosphate, alumina, zirconia, and a composite thereof.

[27] The method according to any of [19] to [26], wherein the ionizing radiation is a gamma ray and/or an electron beam.

[28] The method according to [27], wherein the sterilization by the gamma ray and/or the electron beam is performed under a condition where generation of radical is suppressed, and the condition is one or more conditions selected from the group consisting of (a) sterilization in a degassing state at an atmospheric pressure of 50 kPa, (b) sterilization in a state where air is replaced with a nitrogen or inert gas, (c) sterilization at a low temperature ranging from 0° C. to −196° C., and (d) sterilization in a state where ascorbic acid or ascorbate is further added to the inorganic salt solid into which the protein having bioactivity is embedded.

[29] The method according to [28], wherein the ascorbic acid or ascorbate is selected from the group consisting of ascorbic acid, sodium ascorbate, calcium ascorbate dihydrate, and ascorbic acid phosphate magnesium salt n-hydrate.

[30] The method according to any of [27] to [29], wherein the dose of the gamma ray is 3 to 40 kGy.

[31] The method according to any of [19] to [30], wherein the peptide hormone is one or more peptide hormones selected from the group consisting of a hypothalamus-derived peptide hormone, vasopressin, oxytocin, intermedin, a gonadotrophic hormone, a growth hormone, a parathyroid hormone, inhibin, activin, relaxin, insulin, glucagon, somatostatin, cholecystokinin, secretin, motilin, atrial natriuretic peptide, erythropoietin, leptin, endothelin, ghrelin, adiponectin, an insulin-like growth factor, and calcitonin gene-related peptide.

[32] The method according to any of [19] to [30], wherein the growth factor is one or more growth factors selected from the group consisting of FGF-2 and a functional equivalent thereof.

[33] The method according to any of [19] to [30], wherein the osteogenic protein is one or more osteogenic proteins selected from the group consisting of OP-1, OP-2, BMP-2, BMP-3, BMP-4, BMP-5, BMP-6, BMP-8, BMP-9, DPP, Vg1, Vgr-1, and functional equivalents thereof.

[34] A method of producing a medical instrument for use in tissue repair, the method including the method according to any of [19] to [33].

[35] The method according to [34], wherein the medical instrument for use in tissue repair is one or more medical instruments selected from the group consisting of an intracorporeal fixation pin, an intracorporeal fixation screw, an artificial bone, a bone prosthetic material, a dental endosseous implant, a spinal fixation device, an intramedullary nail, and a spinal cage.

[36] A method of producing a medical instrument for use as an artificial joint, the method including the method according to any of [19] to [33].

Effect of the Invention

The medical instrument of the present invention can avoid an aseptic production process of which process management is complicated, and one aspect thereof relates to a medical instrument sterilized by a terminal sterilization method with radiation (a sterilization method where radiation irradiation is performed in a state where an article to be sterilized is packed in a final package, and where microbial death after such sterilization can be quantitatively measured or estimated).

The medical instrument of the present invention, in which an inorganic salt solid into which a protein having bioactivity is embedded is placed so that a metal, a ceramic or both thereof is partially or entirely coated with the inorganic salt solid, can suppress deactivation of bioactivity of the protein due to radiation sterilization, and thus allows a simple terminal sterilization method with radiation to be applied for various production processes of medical instruments utilizing bioactivity of the protein, and thereby an aseptic production method can be avoided, resulting in a significant decrease in cost.

MODE FOR CARRYING OUT THE INVENTION

Figure 1:
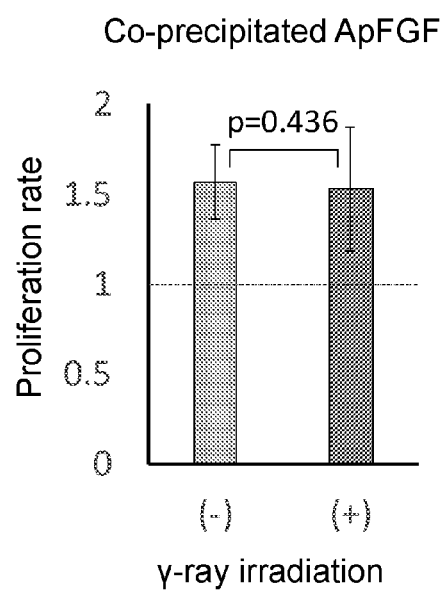
FIG. 1 A graph indicating that, when an external fixation pin made of titanium, for use in bone repair, is coated with FGF-2 embedded into apatite, cell proliferation activity of FGF-2 is kept and protected from radiation deactivation even after gamma-ray irradiation at a dose suitable for sterilization. There is no significant difference between the cell proliferation activity of FGF-2 after gamma-ray irradiation and the cell proliferation activity of FGF-2 not subjected to gamma-ray irradiation.

A medical instrument and a method of producing the medical instrument, provided by the present invention, are respectively a medical instrument for use in mammals including human being, in which an inorganic salt solid into which a protein having bioactivity is embedded is placed so that a metal, a ceramic or both thereof is partially or entirely coated with the inorganic salt solid, and a method of producing the medical instrument, in which
  (a) the inorganic salt solid into which a protein having bioactivity is embedded is provided in a step of controlled delay co-precipitation in a neutral or weak alkaline unstable supersaturated calcium phosphate solution which generates spontaneous nucleation, a coverage sandwich method or a drying method,
  (b) the medical instrument is produced in a step of producing a terminally sterilized medical instrument having one or more bioactivities selected from the group consisting of cell proliferation activity, vascular proliferation activity, soft tissue formation activity, bone tissue formation activity, bone differentiation promotion activity, reaction activity with an antibody, agonistic action activity, and antagonistic action activity, by exposure to ionizing radiation at a dose sufficient for sterilization,
  (c) the inorganic salt is one or more inorganic salts selected from the group consisting of apatite, tricalcium phosphate, octacalcium phosphate, amorphous calcium phosphate, and calcium carbonate, and
  (d) the protein having bioactivity is one or more proteins selected from the group consisting of a peptide hormone, a growth factor, and an osteogenic protein.

The term "embedding" commonly means, as described above, to implant and solidify a living tissue serving as a subject for pathological examination in liquid paraffin or resin which can be solidified, and to thereby fix the living tissue, and the "embedding" herein means to implant the entire protein molecule or a part thereof in an inorganic salt solid, or to cover the entire protein molecule or a part thereof densely with an inorganic salt solid and to fix the protein molecule in the inorganic salt solid. Accordingly, "embedding" is different from a state of simple "adsorption" or "contact" of the protein molecule with the inorganic salt solid, or a state of "mixing" of the protein molecule therewith. An example where the protein molecule is "embedded" into the inorganic salt solid can be a composition where a protein molecule and calcium phosphate are co-precipitated from a supersaturated calcium phosphate solution in which a protein coexists and the protein molecule is arranged in a calcium phosphate matrix with being dispersed at an interval in the order of nanometers (Non-Patent Document 1).

More specifically, the term "embedding" herein encompasses formation of a solid phase by simultaneous crystallization or deposition of both an inorganic salt and a protein molecule from a liquid phase and thus implantation of the entire protein molecule or a part thereof in the inorganic salt solid or covering the entire protein molecule or a part thereof with the inorganic salt solid and fixation of the protein molecule in the inorganic salt solid.

The term "embedding" also similarly encompasses formation of a solid phase by simultaneous crystallization or deposition of both an organic substance such as gelatin and a protein molecule from a liquid phase and thus implantation of the entire protein molecule or a part thereof in the solid organic substance or covering the entire protein molecule or a part thereof by the solid organic substance and fixation of the protein molecule in the solid organic substance.

The term "embedding" should be construed in its broadest sense so as to encompass the above definitions, and should not be construed in a limited way in any sense.

In contrast, the "adsorption" or "contact" means a state obtained by formation of a solid phase of an inorganic salt or an organic substance such as gelatin by crystallization or deposition in advance and thereafter fixation of a protein molecule in a liquid phase to a solid inorganic salt or organic substance. Thus, in a state of simple "adsorption" or "contact" of a protein molecule, a protein molecule fixed is usually specifically present on the surface of the inorganic salt solid or the solid organic substance.

The "mixing" means a state obtained by formation of a solid phase of both an inorganic salt and a protein molecule by crystallization or deposition in advance and thereafter approaching of both the salt and the molecule, or a state obtained by formation of a solid phase of both an organic substance such as gelatin and a protein molecule by crystallization or deposition in advance and thereafter approaching of both the substance and the molecule. Examples of the "mixing" include a state where an inorganic salt powder particle and a protein powder particle coexist in a macroscopically uniform manner, and a state where an organic substance solid powder particle and a protein powder particle coexist in a macroscopically uniform manner.

Whether or not a protein is embedded into an inorganic salt solid can be easily confirmed by, for example, immunoelectron microscopy. In other words, whether or not a protein is embedded into an inorganic salt solid can be confirmed with an electron microscope, by utilizing an antibody labelled with a substance having high electron density, such as gold colloid or ferritin, or a precursor substance thereof and staining and visualizing the protein in the inorganic salt solid for observation under electron microscope. In a case where a protein is embedded into an inorganic salt solid, it can be confirmed that a protein isolated is dispersed and present in an inorganic salt solid matrix (Non-Patent Document 1).

The inorganic salt solid herein means an inorganic salt solid which has biocompatibility so as to be suitable for the medical instrument, specifically, one or more inorganic salts selected from the group consisting of apatite, tricalcium phosphate, octacalcium phosphate, amorphous calcium phosphate, and calcium carbonate.

The inorganic salt solid may be any of a crystalline inorganic salt solid or an amorphous inorganic salt solid. It may also be a state where an amorphous inorganic salt solid and a crystalline inorganic salt solid are mixed, or a state where a plurality of inorganic salt solids different in composition are mixed. Whether the inorganic salt solid is crystalline or amorphous can be easily distinguished generally by a powder X-ray diffraction method, and one broad diffraction halo appears in a powder X-ray diffraction pattern when the inorganic salt solid is completely amorphous, and a plurality of diffraction peaks appear when the inorganic salt solid is crystalline.

The "low crystalline apatite" herein means apatite having low crystallinity, characterized by appearance of three diffraction lines (211), (112), and (300) not separated, in a powder X-ray diffraction pattern, as one peak or diffraction halo. Such three diffraction lines appear with being separated into three lines at positions of diffraction angles of 31.8°, 32.2°, and 32.9°, in measurement with CuKα ray, in the case of apatite with high crystallinity (for example, pure crystalline hydroxyapatite).

Calcium phosphate, calcium carbonate, calcium hydrogen carbonate, sodium phosphate, sodium carbonate, sodium hydrogen carbonate, sodium chloride, apatite, tricalcium phosphate, octacalcium phosphate, and amorphous calcium phosphate may be each a solid solution with any other inorganic element and/or ion group, as impurities. Examples thereof include a solid solution of magnesium in calcium carbonate, a solid solution of carbonic acid in calcium phosphate or sodium phosphate, a solid solution of zinc in calcium phosphate, and a solid solution of potassium in sodium chloride, but are not limited thereto. Examples of such any element and/or ion group in the solid solution can include magnesium, iron, zinc, potassium, hydrogen ion, hydroxide ion, carbonate ion, sulfate ion, and nitrate ion, and the element and/or ion group can be incorporated into the solid solution with the inorganic salt by added to a raw material in embedding.

The protein having bioactivity used herein may be one or more proteins selected from the group consisting of a peptide hormone, a growth factor, and an osteogenic protein. The protein having bioactivity may be a protein which is not recognized as an exogenous substance by any mammal for which the medical instrument is used and which is not biologically rejected by the mammal. For example, the protein encompasses a gene recombinant protein which is artificially prepared based on such a protein intrinsically present in mammals for which the medical instrument is used, and which has similar physiological functions, and a protein which, while modified by a physical or chemical treatment, does not lack essential bioactivity. The term "protein having bioactivity" used herein should not be construed to be in a limited way in any sense, and should be construed in its broadest sense. Examples of the bioactivity may include one or more bioactivities selected from the group consisting of cell proliferation activity, vascular proliferation activity, soft tissue formation activity, bone tissue formation activity, bone differentiation promotion activity, reaction activity with an antibody, agonistic action activity, and antagonistic action activity, but are not limited thereto.

The medical instrument herein means an instrument for use in diagnosis, therapy, and/or prophylaxis of diseases of mammals including human being, and means, for example, an instrument which has an influence on the structure and function of the body of mammals including human being. Mammals herein includes human and non-human mammals, and examples of non-human mammals include monkey, felid animals, canine animals, equine animals, leporid animals, and murine animals such as guinea pig, but are not limited to these particular animals. Some medical instruments are specified by government ordinances, and the medical instrument of the present invention further encompasses those other than the medical instruments specified by government ordinance, such as a mask. Examples include a pacemaker, a coronary artery stent, an artificial blood vessel, a PTCA catheter, a central venous catheter, a bolt for absorbable intracorporeal fixation, and a surgical non-woven fabric, but are not limited to these particular modes. Examples preferably include a medical instrument for use in tissue repair, and a medical instrument for joint function repair, such as an artificial joint, but are not limited thereto. For example, a medical instrument is preferably delivered by surgical stress other than an injection, encompassing needling, and then indwelled. The term "intracorporeal" also encompasses, for example, teeth. The period of indwelling is not particularly limited, and may be, for example, not only temporary indwelling within 24 hours, but also short to medium-term indwelling for about 1 to 30 days or long indwelling for 30 days or more.

Examples of a preferable aspect of the present invention may include an artificial hip joint using a metallic stem, a ceramic bone head, and a liner made of ultrahigh molecular weight polyethylene, in which a metallic stem portion which is to be contacted with the bone is coated with the inorganic salt solid into which the protein having bioactivity is embedded. Other examples thereof may include a metallic screw for bone fixation, in which only a screw head portion is coated with the inorganic salt solid into which the protein having bioactivity is embedded, a dental endosseous implant, in which only a portion of the implant, which is to be contacted with the bone and periodontal tissues, is coated with the inorganic salt solid into which the protein having bioactivity is embedded, a spinal fixation device or a spinal cage, in which only a portion of the device or cage is coated with the inorganic salt solid into which the protein having bioactivity is embedded, a ceramic artificial bone for bone prosthesis, in which the entire artificial bone is coated with the inorganic salt solid into which the protein having bioactivity is embedded, and a composite product of metal and ceramic, in which the entire artificial bone is coated with the inorganic salt solid into which the protein having bioactivity is embedded. It is noted that the scope of the present invention is not limited to these particular aspects.

A method is disclosed which involves co-precipitating a physiologically active substance with an inorganic salt to thereby coat a substrate with the co-precipitate and sterilizing the resultant with gamma-ray irradiation at the final stage (Patent Document 19), but this Document neither describes nor indicates the remaining of particular bioactivity of the physiologically active substance after sterilization and furthermore an optimal substrate allowing particular bioactivity of the physiologically active substance to remain after sterilization. The present inventors have found that, although bioactivity of a physiologically active substance hardly remains after sterilization in the case of coating of a substrate with a polymer material, and that particular bioactivity of protein highly remains after ionizing radiation sterilization by coating a metal or ceramic substrate with an inorganic salt solid into which the protein having bioactivity is embedded.

While the ceramic means a non-metal inorganic solid material made by an artificial heat treatment in a narrow sense, a non-metal inorganic solid material not subjected to any heat treatment available in the medical and medical instrument fields is also herein called "ceramic". The ceramic may be herein a non-metal inorganic solid material, and encompasses one obtained by any preparation method, for example, one prepared by an artificial heat treatment and one prepared without any heat treatment.

A preferable aspect of the present invention provides, for example, a medical instrument including a structure placed so that a metal for transplantation, a ceramic for transplantation, or both thereof is partially or entirely coated with an inorganic salt solid into which not only a protein having bioactivity, but also polysaccharide, preferably heparin, is embedded, as well as a method of producing the medical instrument. A polysaccharide derived from an extracellular matrix, such as heparin, is valuable because it contributes to maintaining bioactivity of a protein having bioactivity, while the polysaccharide itself is a biological polymer having no direct cell proliferation/differentiation activity.

A preferable aspect of the present invention provides, for example, a medical instrument including a structure placed so that a metal for transplantation, selected from the group consisting of titanium, a titanium alloy, stainless steel, and a cobalt/chromium alloy, is partially or entirely coated with an inorganic salt solid into which a protein having bioactivity is embedded, as well as a method of producing the medical instrument. Titanium, a titanium alloy, stainless steel, and a cobalt/chromium alloy are each a metal with high biocompatibility and widely used in orthopedics and/or dentistry, and thus are each valuable as a medical instrument in the orthopedic and dentistry fields.

Another further preferable embodiment of the present invention provides a medical instrument placed so that a ceramic for transplantation, selected from the group consisting of apatite, tricalcium phosphate, octacalcium phosphate, amorphous calcium phosphate, and a composite thereof, is partially or entirely coated with an inorganic salt solid into which a protein having bioactivity is embedded, as well as a method of producing the medical instrument. The ceramic for transplantation may include, for example, alumina and/or zirconia. These ceramics are also materials with high biocompatibility and widely used in orthopedics and/or dentistry, and thus are valuable as a medical instrument in the orthopedic and dentistry fields. These ceramics also encompass a solid solution of other inorganic element and/or ion group as impurities. Examples thereof include a solid solution of carbonic acid or silicon in apatite, a solid solution of silicon in tricalcium phosphate, a solid solution of magnesium in amorphous calcium phosphate, and a solid solution of yttrium in zirconia, but are not limited thereto. Examples of the composite may include a biphasic ceramic made of apatite and tricalcium phosphate, and a composite ceramic of alumina and zirconia, but are not limited to these particular modes.

The medical instrument comprising an inorganic salt solid into which a protein having bioactivity is embedded can be sterilized at a sufficient dose of ionizing radiation for sterilization with maintaining the activity of the bioactive protein substantially, and thus can be a medical instrument terminally sterilized.

The ionizing radiation for use in sterilization is preferably a gamma ray and/or an electron beam. By utilizing the gamma ray which easily penetrates through a substance, the inorganic salt solid into which the protein having bioactivity is embedded can be easily sterilized. For example, a portion of the protein embedded into the inorganic salt solid, the portion being exposed on the surface of the solid, can also be sterilized by electron beam irradiation according to a method well-known by those skilled in the art. By packaging the entire medical instrument appropriately and thus sealed at first, and thereafter irradiating gamma ray or electron beam by a method well-known by those skilled in the art, a product in which the medical instrument sterilized is sealed and included can be obtained, and the product can be provided as a medical instrument aseptically sealed and packaged, to the medical workplace (Non-Patent Document 17). Aspects of the present invention are not limited to these particular aspects.

The dose necessary for sterilization may be typically minimum dose necessary for ensuring a sterility assurance level (SAL) of $10^{-6}$. The sterility assurance level is prescribed by the standard such as ISO (ISO 11137-1, 1137-2) and JIS (JIS T 0806-1, 0806-2), and is adopted by the regulatory agency of each country, for example, FDA in U.S.A and PMDA (Pharmaceuticals and Medical Devices Agency) in Japan.

In a case where a gamma ray is used for sterilization, for example, a dose of about 10 to 40 kGy, preferably 15 to 30 kGy may be selected as the dose for ensuring a sterility assurance level of $10^{-6}$ and sterilizing the medical instrument of the present invention. The dose of radiation for achieving the sterility assurance level may be preferably about 25 kGy. It is noted that the dose is not limited to such a particular dose of radiation.

In another further preferable embodiment of the present invention, sterilization may be performed in a degassing state at an atmospheric pressure of 50 kPa or less, preferably less than 50 Pa, further preferably 20 Pa or less in order to suppress the generation of radical in the sterilization step with a gamma ray and/or an electron beam. Alternatively, sterilization is also preferably performed in a state where air is replaced with a nitrogen or inert gas. Furthermore, sterilization may also be preferably performed at a low temperature of 0° C. to −196° C., preferably −20° C. to −80° C., further preferably −20° C. to −80° C. under the coexistence of dry ice. Alternatively, sterilization may also be preferably performed after addition of ascorbic acid or ascorbate to the inorganic salt solid into which the protein is embedded. Uniform dispersion and addition of ascorbic acid or ascorbate can be achieved by immersion in a solution of 5 to 50 mM, preferably 10 to 30 mM of ascorbic acid or ascorbate and then drying, but is not limited thereto.

One preferable embodiment of the present invention, from another viewpoint, provides a medical instrument for use in mammals, comprising an inorganic salt solid into which a peptide hormone selected from the group consisting of a hypothalamus-derived peptide hormone, vasopressin, oxytocin, intermedin, a gonadotrophic hormone, a growth hormone, a parathyroid hormone, inhibin, activin, relaxin, insulin, glucagon, somatostatin, cholecystokinin, secretin, motilin, atrial natriuretic peptide, erythropoietin, leptin, endothelin, ghrelin, adiponectin, an insulin-like growth factor, and calcitonin gene-related peptide is embedded, and a method of producing the medical instrument.

Another preferable aspect provides a medical instrument for use in mammals, comprising an inorganic salt solid into which an FGF-2 (fibroblast growth factor-2) is embedded as a growth factor, and a method of producing the medical instrument. FGF-2 is a growth factor useful for soft tissue regeneration, blood vessel formation, and bone formation, and thus such a medical instrument is useful for an application where tissue regeneration is promoted.

Still another preferable embodiment provides a medical instrument for use in mammals, comprising an inorganic salt solid into which one or more osteogenic proteins selected from the group consisting of OP-1, OP-2, BMP-2, BMP-3, BMP-4, BMP-5, BMP-6, BMP-8, BMP-9, DPP, Vg1, Vgr-1, and functional equivalents thereof is/are embedded as osteogenic protein(s), and a method of producing the medical instrument. Such a medical instrument is useful for an application where tissue regeneration is promoted.

One preferable embodiment of the present invention, from still another viewpoint, provides a medical instrument in which bioactivity of a protein having bioactivity is bioactivity selected from the group consisting of cell proliferation activity, vascular proliferation activity, soft tissue formation activity, bone tissue formation activity, bone differentiation promotion activity, reaction activity with an antibody, and agonistic action activity, and a method of producing the medical instrument. The bioactivity in the protein or the medical instrument can be evaluated by the number of cells in cell culturing, a differentiation marker, a substance produced, gene expression, a cell form, and/or the collective form of cells, for example, formation of a vascular-like structure. In animal testing, the bioactivity can be evaluated by, for example, observation of a tissue form with a tissue specimen, a tissue image by X-ray, MRI, or the like, and/or gene expression. In a case where the protein having bioactivity behaves as an antigen, an agonist, or an antagonist, the bioactivity can be evaluated by any of various methods such as western blotting with a monoclonal antibody involving a bioactive moiety of the protein or a monoclonal antibody labelled. In a case where the protein having bioactivity is an antibody, the bioactivity can be evaluated by labelling the antibody in advance and then binding it to an antigen, and evaluating the amount and binding activity of the antibody bound to the antigen, by utilizing the activity and amount of such a substance labelled. In a case where the protein having bioactivity is an enzyme, the bioactivity can also be evaluated by using an enzymatic substrate and evaluating a reaction product derived from the enzymatic substrate by an enzyme. It is noted that the evaluation method is not limited thereto as long as it can evaluate the particular bioactivity to be evaluated. Any evaluation method can verify whether or not the protein and the medical instrument have bioactivity, by, for example, comparison of the particular bioactivity between a group of the inorganic salt solid including the protein and a group of the inorganic salt solid including no protein. As samples for bioactivity comparison between both the groups, the inorganic salt solid, the medical instrument or the graft containing or not containing the protein can be used as it is or as in the form of an extraction liquid obtained by dissolving the inorganic salt solid with an appropriate extraction liquid and thus extracting the protein.

A procedure for quantitative evaluation, utilizing the above bioactivity and the evaluation method thereof, can be used in order to evaluate the bioactivity of the medical instrument sterilized by ionizing radiation at a dose sufficient for sterilization. The medical instrument of the present invention has at least about 13% or more, preferably 65% or more, further preferably 70% or more of bioactivity relative to that before sterilization, after sterilization for ensuring a sterility assurance level of $10^{-6}$.

As a preferable method of embedding the protein having bioactivity into the inorganic salt solid, for example, a co-precipitation deposition method using a sodium chloride solution, a sodium phosphate solution, a carbonate ion-containing calcium solution, a sodium carbonate solution, or a sodium hydrogen carbonate solution, a coverage sandwich method, or a drying method may be adopted.

The co-precipitation deposition method is a method wherein a desired bioactive protein is allowed to coexist in a desired supersaturated inorganic salt solution and a crystal or amorphous solid of the inorganic salt is deposited from the supersaturated solution with capturing the protein or densely surrounding the protein molecule by the inorganic salt solid. The co-precipitation deposition is also a method where a crystal or amorphous solid of the inorganic salt into which the protein is embedded is deposited so that another solid surface is coated therewith.

The coverage sandwich method is a method involving allowing a desired bioactive protein to adsorb to or contact with a surface of a desired inorganic salt solid in advance, and covering the surface with the same one as or different one from the inorganic salt solid into which the bioactive protein is embedded. Other methods may include a drying method in which, for example, the protein can be densely embedded into the inorganic salt solid by dissolving a desired bioactive protein in a desired inorganic salt solution and freeze-drying or concentrating and drying the solution. Such a method can be adopted singly or in appropriate combination of two or more kinds thereof, or may be, if necessary, repeated for an appropriate number of times. By performing these methods, a plurality of layers each including a composition of the protein embedded into the inorganic salt solid can be placed, preferably in a state where a desired bioactive protein can be protected from radiation sterilization. The inorganic salt solid thus produced, into which the bioactive protein is embedded, is obtained as a precipitate from the solution or in the state of being suspended in the solution, and can also be obtained as a layer coating a metal for transplantation or a ceramic for transplantation, as described above, and can be appropriately separated from the solution and then dried.

As a preferable method of embedding the protein having bioactivity into the inorganic salt solid a co-precipitation deposition method involving controlled delay co-precipitation of the protein having bioactivity and calcium phosphate in an unstable supersaturated calcium phosphate solution which uses a neutral or weak alkaline solution and which generates spontaneous nucleation, or a coverage sandwich method. As a method of co-precipitating a protein and calcium phosphate at a desired time point by suppressing spontaneous nucleation, crystallization, or precipitation of calcium phosphate in a protein-containing high-concentration calcium phosphate solution and thus stabilizing the solution at a high concentration as it is, a method involving decreasing the pH by bubbling of carbon dioxide and/or addition of acid to thereby decrease the degree of super-saturation to result in complete dissolution and then gradually increasing the pH by degassing of carbon dioxide, addition of alkali, or OH— ion generation by electrochemical reduction of a water molecule to thereby increase the degree of supersaturation, and gradually crystallizing calcium phosphate to thereby allow co-precipitation with the protein (Patent Document 19, Patent Document 25, Patent Document 26, Patent Document 27, and Patent Document 33). The method is considered to allow co-precipitation to occur, by increasing the pH of a stable supersaturated calcium phosphate solution which is acidic and completely dissolved and which generates no spontaneous nucleation, to thereby increase the degree of supersaturation.

However, many proteins have the problem of being denatured and thus lose their activity at an acidic pH or a high-alkaline pH. In order to avoid this problem, a solution where a large amount of K ion or Na ion is added to a neutral or weak alkaline high-concentration calcium phosphate solution which may rapidly form a large amount of a precipitate is prepared as an unstable supersaturated calcium phosphate solution which generates spontaneous nucleation, the time until crystallization is delayed by an increase in activation energy of crystallization and thus a decrease in frequency of nucleation, and calcium phosphate is gradually crystallized to enable co-precipitation with a protein to occur. This method is a method of performing controlled delay co-precipitation of a protein having bioactivity and calcium phosphate by not adjusting the degree of supersaturation of the solution, but by changing the activation energy of crystallization, and, more specifically, delay co-precipitation can be performed by adjusting the KCl concentration, which does not relate to the concentration of calcium phosphate, pH, and the degree of supersaturation, and controlling and extending the time until spontaneous nucleation.

For example, the above delay co-precipitation is preferably performed by using an aqueous solution including 0.5 to 2.5 mM of Ca ion, 1.0 to 20 mM of phosphate ion, 0 to 40 mM of K ion, 0 to 200 mM of Na ion, and 0 to 200 mM of Cl ion, and having a pH of 7.0 to 9.0, preferably an aqueous solution including 1.2 to 2.75 mM of Ca ion, 0.6 to 15 mM of phosphate ion, 0 to 30 mM of K ion, 30 to 150 mM of Na ion, 0.1 to 3.0 mM of Mg ion, 30 to 150 mM of Cl ion, and 0 to 60 mM of $HCO_3$ ion, and having a pH of 7.0 to 9.0, as the unstable supersaturated calcium phosphate solution, and controlling the KCl concentration in the aqueous solution to thereby artificially control and delay the time until calcium phosphate deposition. Since Mg ion and $HCO_3$ ion are inhibitors of calcium phosphate crystallization, an unstable supersaturated calcium phosphate solution to which not only K ion and Na ion, but also Mg ion and $HCO_3$ ion are added can allow the time until calcium phosphate deposition to be further controlled and delayed artificially (Patent Document 29).

EXAMPLES

Hereinafter, the present invention will be more specifically described with reference to Examples, but the scope of the present invention is not limited to the following Examples. The terms and concepts in the Examples are based on the terms conventionally used in the art, and any technique for carrying out the present invention, except for any technique whose reference is specifically and clearly shown, can be easily and certainly carried out by those skilled in the art based on a known document or the like. Various analyses and the like are performed using methods described in instructions, catalogs, and the like of analysis instruments, reagents, or kits used.

Example 1

Cell Proliferation Activity after Radiation Sterilization of External Fixation Pin Coated with Apatite into which FGF-2 was Embedded A titanium pin for intracorporeal fixation, which may be used for fracture fixation, was coated with an inorganic salt solid into which FGF-2 having cell proliferation activity was embedded, the resultant was entirely subjected to ionizing radiation sterilization, and thereafter whether or not FGF-2 had cell proliferation activity was examined.

An unstable supersaturated calcium phosphate solution including 4.89 mM of Ca ion, 1.28 mM of phosphate ion, 6.13 mM of K ion, 138.8 mM of Na ion, 0.23 mM of Mg ion, 136.6 mM of Cl ion, and 15.09 mM of $HCO_3$ ion, and having a pH of 7.8, in which calcium phosphate would be crystallized by spontaneous nucleation in about 4 to 5 hours if the solution was left at 37° C. as it was, was used (this unstable supersaturated calcium phosphate solution was different from the liquid of Patent Document 19). Fibroblast growth factor-2 (FGF-2) was added at each of concentrations of 4 µg/ml and 0 µg/ml to the unstable supersaturated calcium phosphate solution. A titanium pin for intracorporeal fixation (DePuy Synthes, cell drill 4.0/3.0 mm Ti, 20 mm-80 mm) was immersed therein at 37° C. for 48 hours, and coated with FGF-2 by co-precipitated with apatite, to thereby produce each of 6 or 8 co-precipitated apatite FGF-2 (co-precipitated ApFGF) pins. Similarly, FGF-2-free unstable supersaturated calcium phosphate solution was used to produce each of 6 or 8 Ap pins. The co-precipitated ApFGF pins produced were each loaded into a tube and vacuum-dried at 12.4 Pa at room temperature for 2 hours. The lid of the tube receiving each of the pins was closed immediately after the drying, and each of the pins was packaged by using an anaerobic-dry storage system (I.S.O.) composed of a gas-shielding storage bag, an oxygen absorbing agent, and a synthetic zeolite drying agent.

Half these ApFGF pins were subjected to γ-ray irradiation at a dose of 25±0.5 kGy with $^{60}Co$ as a radiation source. The irradiation was performed at ordinary temperature, and the pins were stored at 4° C. also over a transport period. The co-precipitated ApFGF pins not subjected to γ-ray irradiation were stored at 4° C. In order to evaluate the cell proliferation activity of FGF-2 supported on each of the co-precipitated ApFGF pins including the pins subjected to γ-ray irradiation and the pins not subjected to γ-ray irradiation, these pins were each immersed and dissolved in a 10 mM sodium citrate solution for 30 minutes. An FGF-2-free Ap pin as a control was also immersed in a 10 mM sodium citrate solution for 30 minutes to thereby dissolve a coating layer. Since calcium in the dissolution liquid could promote cell proliferation, the samples were uniformed in terms of the calcium concentration after ICP emission spectrometric analysis, and each added to mouse fibroblast strains NIH3T3, and the proliferation rate was measured using Cell Counting Kit-8. The proliferation rate of the FGF-2-free Ap pin as a control was defined as 1, and any co-precipitated ApFGF pin showing statistically significantly high proliferation rate was rated as "having activity". An operation including coating by co-precipitation, vacuum-drying, γ-ray irradiation or no γ-ray irradiation, and measurement of the proliferation rate was repeatedly trialed four times.

Table 1 shows the number of co-precipitated ApFGF pins rated as "having activity" in the four repeated trials. FIG. 1 illustrates the values of the proliferation rates measured.

TABLE 1

| | Co-precipitated ApFGF | |
|---|---|---|
| Number of trials | γ-ray (−) | (+) |
| First trial | 4/4 | 4/4 |
| Second trial | 0/3 | 0/3 |
| Third trial | 3/3 | 3/3 |
| Fourth trial | 3/3 | 3/3 |
| Total (pins) | 10/13 | 10/13 |

As shown in Table 1, 10 pins/13 pins in the γ-ray irradiation group of the co-precipitated ApFGF pins, and 10 pins/13 pins in the no irradiation group thereof were rated as "having cell proliferation activity", and the number of such pins each having cell proliferation activity was the same between the γ-ray irradiation group and the no irradiation group, in the four repeated trials. As illustrated in FIG. 1, the co-precipitated ApFGF pins not only in the γ-ray irradiation group, but also in the no irradiation group each exhibited a proliferation rate about 1.5 times higher than that of the Ap pin, the proliferation rate in the no γ-ray irradiation group was statistically significantly higher than the proliferation rate (proliferation rate=1) of the Ap pin (p=0.021), and the difference between the proliferation rate in the γ-ray irradiation group and the proliferation rate (proliferation rate 1) of the Ap pin was extremely close to a significant level (p=0.058). No significant difference (p=0.436) was confirmed between the proliferation rate in the irradiation group and that in the no irradiation group. In other words, it was revealed that, in a case where the intracorporeal fixation pin made of titanium as a metal for transplantation was coated with the composition where FGF-2 was embedded into apatite, the protein attained ionizing radiation sterilization resistance by embedding, namely, embedding into apatite exhibited radioprotective effect on the bioactive protein. Herein, because embedding into apatite exhibited radioprotective effect on the bioactive protein in a condition of gamma-ray irradiation at 25±0.5 kGy, such radioprotective effect would be exhibited also against gamma-ray irradiation at less than 25±0.5 kGy.

Example 2

Cell Proliferation Activity after Radiation Sterilization of External Fixation Pin Coated with Apatite to which FGF-2 was Adsorbed Titanium pins for intracorporeal fixation, which may be used for fracture fixation, were coated with an inorganic salt solid to which FGF-2 having cell proliferation activity was adsorbed, the resultants were entirely subjected to ionizing radiation sterilization, and thereafter whether or not FGF-2 had cell proliferation activity was examined.

An FGF-2-free supersaturated calcium phosphate solution was prepared using the same unstable supersaturated calcium phosphate solution as in Example 1, and 6 or 8 titanium pins for intracorporeal fixation (DePuy Synthes, cell drill 4.0/3.0 mm Ti, 20 mm-80 mm) were immersed therein at 37° C. for 48 hours, to thereby produce respective Ap pins whose surfaces were coated with apatite. The Ap pins were immersed in a supersaturated calcium phosphate solution containing 12 μg/ml of FGF-2 for several seconds, and frozen at −18° C., to thereby produce adsorbed apatite FGF-2 (adsorbed ApFGF) pins each coated with apatite to which FGF-2 was adsorbed. The pins were vacuum-dried at room temperature, subjected or not subjected to γ-ray irradiation, stored, and evaluated with respect to cell proliferation activity in the completely same conditions as in Example 1. An operation including coating with apatite to which FGF-2 was adsorbed, γ-ray irradiation or no γ-ray irradiation, and measurement of the proliferation activity was repeatedly trialed five times.

Figure 2:
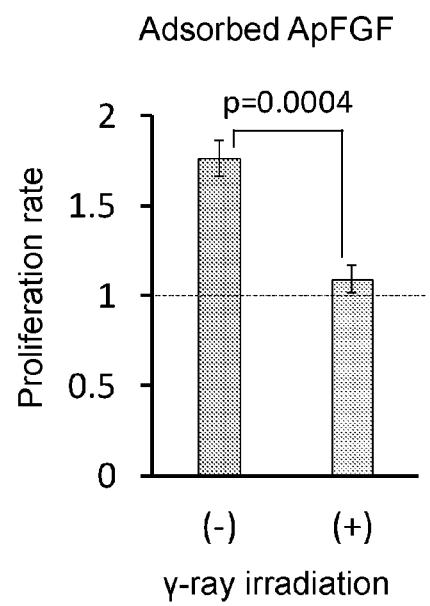
FIG. 2 A graph indicating that, when FGF-2 is absorbed to an external fixation pin made of titanium, for use in bone repair, coated with apatite, cell proliferation activity of FGF-2 is disappeared and not protected from radiation deactivation after gamma-ray irradiation at a dose suitable for sterilization. The cell proliferation activity of FGF-2 after gamma-ray irradiation is statistically significantly lower than the cell proliferation activity of FGF-2 not subjected to gamma-ray irradiation.

Table 2 shows the number of adsorbed ApFGF pins rated as "having activity" in the five repeated trials. FIG. 2 illustrates the values of the proliferation rates measured.

TABLE 2

| Number of trials | Adsorbed ApFGF | |
|---|---|---|
| | (−) | (+) |
| First trial | 3/4 | 0/4 |
| Second trial | 3/3 | 0/3 |
| Third trial | 0/3 | 0/3 |
| Fourth trial | 2/3 | 1/3 |
| Fifth trial | 3/3 | 1/3 |
| Total (pins) | 11/16 | 2/16 |

As shown in Table 2, 2 pins/16 pins in the γ-ray irradiation group of the adsorbed ApFGF pins, and 11 pins/16 pins in the no irradiation group thereof were rated as "having cell proliferation activity", and the number of pins having cell proliferation activity in the γ-ray irradiation group was about one-fifth of the no irradiation group, in the five trials. Both the groups were subjected to the chi-square test, and a significant difference (p=0.001) was recognized between the γ-ray irradiation group and the no irradiation group and thus it was revealed that the adsorbed ApFGF pin lost bioactivity of FGF-2 by γ-ray irradiation sterilization. As illustrated in FIG. 2, while the adsorbed ApFGF pin in the no irradiation group exhibited a proliferation rate about 1.7 times (p=0.003) higher than that exhibited by the Ap pin, the proliferation rate exhibited by the adsorbed ApFGF pin in the γ-ray irradiation group was decreased to 1.1 times higher than that exhibited by the Ap pin and no significant difference from that exhibited by the Ap pin was recognized (p=0.087), and it was revealed that the cell proliferation rate of FGF-2 significantly (p=0.0004) disappeared by about 35% by γ-ray irradiation. In contrast, as illustrated in FIG. 1 described above, the co-precipitated ApFGF pins in both the γ-ray irradiation group and the no irradiation group each exhibited a proliferation rate about 1.5 times higher than that exhibited by the Ap pin, and no significant difference (p=0.436) was recognized between the irradiation group and the no irradiation group. In other words, while Patent Documents 12, 13 and 17 describe radiation sterilization of a composition of a combination of a protein having bioactivity and an inorganic salt, modes of such a combination include "mixing", "adsorption", "contact", and "embedding", and it has been found that the difference in combination mode leads to a large difference in protein bioactivity after terminal sterilization and a mode "embedding" allows such protein bioactivity to be maintained at a high efficiency.

Example 3

Cell Proliferation Activity after Radiation Sterilization of External Fixation Pin Coated with Gelatin into which FGF-2 was Embedded The titanium pins for intracorporeal fixation, as within Example 1, were immersed in a 1% gelatin solution containing 4 μg/ml of FGF-2 for several seconds, and frozen at −18° C., to thereby produce pins (gelatin FGF) coated with gelatin into which FGF-2 was embedded. The pins were vacuum-dried at room temperature, subjected to or not subjected to γ-ray irradiation, stored, and evaluated with respect to cell proliferation activity, in the completely same conditions as in Example 1. An operation including coating with gelatin into which FGF-2 was embedded, γ-ray irradiation or no γ-ray irradiation, and measurement of the proliferation rate was repeatedly trialed four times.

Figure 3:
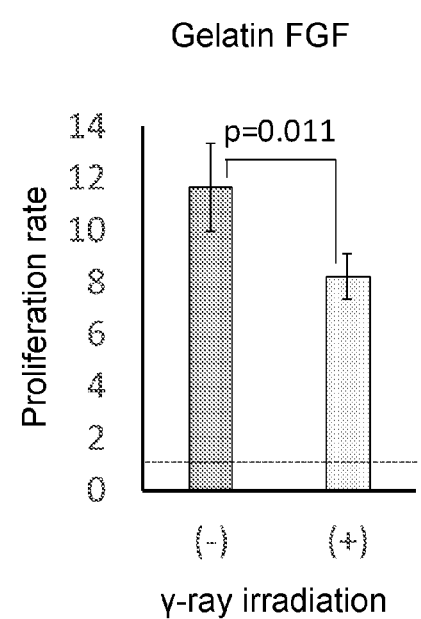
FIG. 3 A graph indicating that, when an external fixation pin made of titanium, for use in bone repair, is coated with FGF-2 embedded into gelatin, cell proliferation activity of FGF-2 is disappeared and not protected from radiation deactivation after gamma-ray irradiation at a dose suitable for sterilization. The cell proliferation activity of FGF-2 after gamma-ray irradiation is statistically significantly lower than the cell proliferation activity of FGF-2 not subjected to gamma-ray irradiation.

Table 3 shows the number of gelatin FGF pins rated as "having activity" in the four repeated trials. FIG. 3 illustrates the values of the proliferation rates measured.

TABLE 3

| Number of trials | Gelatin FGF | |
|---|---|---|
| | (−) | (+) |
| First trial | 4/4 | 4/4 |
| Second trial | 3/3 | 3/3 |
| Third trial | 3/3 | 3/3 |
| Fourth trial | 3/3 | 3/3 |
| Total (pins) | 13/13 | 13/13 |

As shown in Table 3, 13 pins/13 pins in the γ-ray irradiation group of the gelatin FGF pins each coated with gelatin into which FGF-2 was embedded, and 13 pins/13 pins in the no irradiation group thereof were rated as "having cell proliferation activity", and the number of such pins each having cell proliferation activity was the same between the γ-ray irradiation group and the no irradiation group, in the four repeated trials. However, as illustrated in FIG. 3, while the gelatin FGF pin in the no irradiation group exhibited a proliferation rate about 12 times higher than that exhibited by the Ap pin, the proliferation rate exhibited by the gelatin FGF pin in the γ-ray irradiation group was decreased to about 8 times higher than that exhibited by the Ap pin, and it was revealed that the cell proliferation rate of FGF-2 statistically significantly ($p=0.011$) disappeared by about 30% by γ-ray irradiation. In other words, it was found that, in a case where a matrix into which the protein having bioactivity was embedded was an organic substance such as gelatin, radioprotective effect was low unlike cases of Example 1 and FIG. 1 where a matrix for embedding was the inorganic salt solid. Patent Document 18 describes a carrier sterilized after synthesis, in which bioactivity is incorporated into a carrier matrix including an inorganic, organic, or organic and inorganic substance, but does not indicate which combination or material of the carrier matrix including an inorganic, organic, or organic and inorganic substance allows bioactivity to be maintained even after sterilization, or which sterilization method allows bioactivity to be maintained even after sterilization. It is revealed in Examples of the present invention that a case where the protein having bioactivity is embedded into a matrix of the inorganic salt solid exhibits much excellent radioprotective effect as compared with a case where the protein is embedded into an organic matrix. The reason is considered that the organic substance may generate many radicals by radiation irradiation unlike the inorganic salt solid.

Example 4

Cell Proliferation Activity after Radiation Sterilization of Apatite Ceramic for Artificial Bone, Coated with Apatite into which FGF-2 was Embedded A hydroxyapatite powder containing 3% of polyvinyl alcohol and having a size of 70 microns or less was press-molded and sintered at 1150° C. for 1 hour, to thereby produce dense discs made of apatite (ellipse of 5 mm diameter×3 mm width×1 mm thickness). The production method was essentially the same as the method of producing the apatite ceramic for artificial bone. The discs made of apatite were coated with co-precipitated ApFGF and the resultants were vacuum-dried and subjected to γ-ray irradiation according to the same method as in Example 1, and thereafter NIH3T3 cells were cultured on the disc and the cell proliferation rate was measured. In a case where NIH3T3 cells were cultured directly on the disc, the adhesiveness of the cells changes by the influence of the protein, therefore a disc made of apatite in a no irradiation group, as a control, was immersed in an unstable supersaturated calcium phosphate solution to which bovine serum albumin (BSA) was added instead of FGF-2, and coated with ApBSA. An operation including coating, γ-ray irradiation or no γ-ray irradiation, and measurement of the proliferation rate was repeatedly trialed three times.

Figure 4:
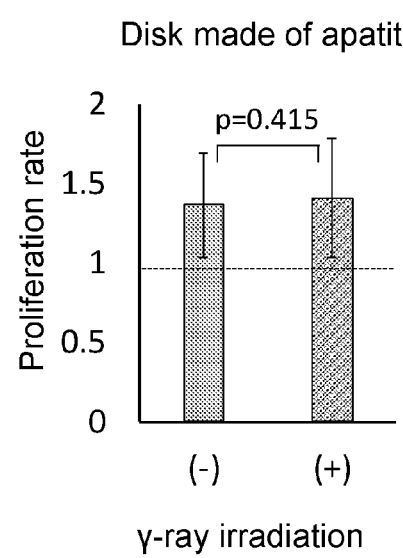
FIG. 4 A graph indicating that, when coating with FGF-2 embedded into apatite and irradiating gamma-ray at a dose suitable for sterilization, ceramics for transplantation can be used in a member of a medical instrument where cell proliferation activity of FGF-2 is to be maintained. There is no significant difference between the cell proliferation activity of FGF-2 after gamma-ray irradiation and the cell proliferation activity of FGF-2 not subjected to gamma-ray irradiation.

Table 4 shows the number of discs made of co-precipitated ApFGF apatite, rated as "having activity" in the three repeated trials. FIG. 4 illustrates the values of the proliferation rates measured.

TABLE 4

|  | Disc made of apatite | |
| --- | --- | --- |
| Number of trials | γ-ray (−) | (+) |
| First trial | 6/6 | 6/6 |
| Second trial | 6/6 | 6/6 |
| Third trial | 6/6 | 6/6 |
| Total (discs/discs) | 18/18 | 18/18 |

As shown in Table 4, 18 discs/18 discs in the γray irradiation group of the discs made of co-precipitated ApFGF apatite, and 18 discs/18 discs in the no irradiation group thereof were rated as "having cell proliferation activity", and the number of such discs made of apatite, each having cell proliferation activity, was the same between the γ-ray irradiation group and the no irradiation group, in the three trials. As illustrated in FIG. 4, the discs made of co-precipitated ApFGF apatite in both the γ-ray irradiation group and the no irradiation group each exhibited a proliferation rate about 1.4 times higher than that exhibited by the Ap pin, and no significant difference ($p=0.415$) was recognized between the irradiation group and the no irradiation group. In other words, it was revealed that, in a case where a ceramic for transplantation was coated with the composition where FGF-2 was embedded into apatite, the protein attained ionizing radiation sterilization resistance by embedding, namely, embedding into apatite exhibits radioprotective effect on the bioactive protein, like a case where a metal for transplantation was coated.

Example 5

Cell Proliferation Activity after Radiation Sterilization of Polymer Coated with Apatite into which FGF-2 was Embedded Round bars made of polyether ether ketone (PEEK) (6 mm diameter×8 cm length) as a polymer were used, and the surfaces thereof were coated with co-precipitated ApFGF and the resultants were vacuum-dried and subjected to γ-ray irradiation or no irradiation, stored, and measured with respect to the cell proliferation rate, in the same conditions as in Example 1. Polyether ether ketone is a polymer which may be used in transplantation.

Table 5 shows the number of round bars made of co-precipitated ApFGF-PEEK, rated as "having activity", in the three repeated trials.

TABLE 5

|  | PEEK | |
| --- | --- | --- |
| Number of trials | (−) | (+) |
| First trial | 3/3 | 1/3 |
| Second trial | 3/3 | 3/3 |
| Third trial | 3/3 | 2/3 |
| Total (bars/bars) | 9/9 | 6/9 |

As shown in Table 5, 6 bars/9 bars in the γ-ray irradiation group of the co-precipitated ApFGF-PEEK round bars, and 9 bars/9 bars in the no irradiation group thereof were rated as "having cell proliferation activity", and the number of pins having cell proliferation activity in the γ-ray irradiation group was two-thirds of the no irradiation group, in the three trials. It was revealed that bioactivity of FGF-2 in the co-precipitated ApFGF-PEEK round bar disappeared by γ-ray irradiation sterilization. Patent Document 19 describes a method of obtaining a substrate coated, by contacting a substrate with an acidified composition including a brine mixture including calcium, magnesium, phosphoric acid, hydrogen carbonate ion and a bioactive substance, to result in an increase in pH and thereby generate co-precipitation of a salt and the bioactive substance. Although there is no mention in the invention recited in claims, the specification describes that gamma-ray irradiation can also be performed after the last step. However, it is revealed in Examples of the present invention that, in a case where the protein having bioactivity is co-precipitated on a polymer for transplantation to thereby coat the polymer therewith, no sufficient radioprotective effect can be achieved and a case of co-precipitation on and coating of a metal or ceramic for transplantation exhibits much excellent radioprotective effect. The reason is considered that the polymer may generate many radicals by radiation irradiation unlike the metal or ceramic.

Example 6

Influence of Atmosphere in Radiation Sterilization, on Bioactivity of Protein Embedded into Inorganic Salt Solid Titanium pins for external fixation, as a metal for transplantation, were coated with apatite into which FGF-2 was embedded, in the same conditions as in Example 1 and the resultant was subjected to γ-ray irradiation at a dose of 25±0.5 kGy, and how the atmosphere in the γ-ray irradiation influences on FGF-2 having reaction activity with an anti-FGF-2 antibody was examined.

Co-precipitated ApFGF pins were produced using titanium pins for intracorporeal fixation in the same manner as in Example 1, and sealed and packaged. Here, three atmosphere conditions of (i) the same anaerobic-dry packaging as in Example 1, (ii) degassing packaging, and (iii) nitrogen packing packaging were applied. The degassing was performed as a vacuum degassing treatment at 29.2 kPa for 5 seconds. Nitrogen replacement was performed by allowing a high-purity nitrogen gas to flow in. Thereafter, γ-ray irradiation was performed at a dose of 25±0.5 kGy. A co-precipitated ApFGF pin not subjected to γ-ray irradiation (no irradiation group) in the same anaerobic-dry packaging as in Example 1 was adopted as a control. The co-precipitated ApFGF pin not subjected to γ-ray irradiation was immersed in a 10 mM sodium citrate solution for 30 minutes to thereby dissolve a coating layer, and FGF-2 supported on the pin was detected by western blotting using an anti-FGF-2 antibody. A dissolution liquid was concentrated to 20-fold by freeze-drying and then subjected to western blotting. The antibody here used was a human FGF-2 mouse monoclonal antibody (Thermo Fisher Scientific) involving in bioactivity of FGF-2. Image data acquired was used for quantitative determination and comparison of a signal intensity detected at a position of 17 kDa (molecular weight of FGF-2: 17,000) with Image Lab (Bio-Rad Laboratories, Inc.).

Figure 5:
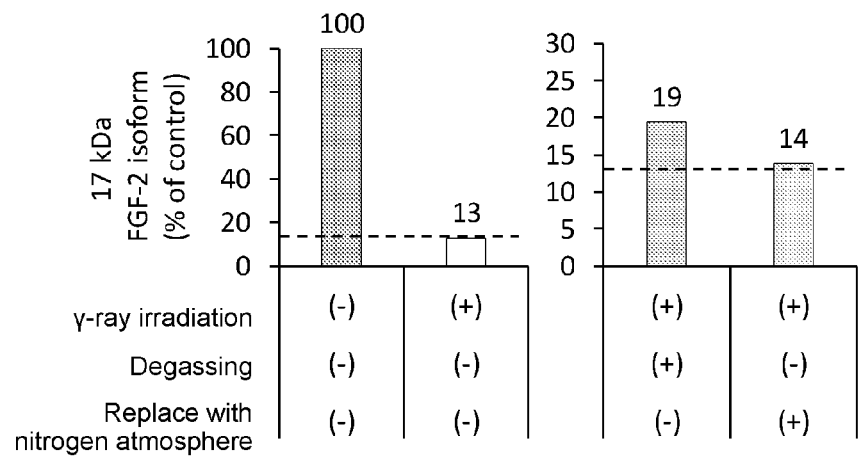
FIG. 5 A graph indicating that, when an external fixation pin made of titanium, for use in bone repair, is coated with FGF-2 embedded into apatite and gamma-ray is irradiated at a dose suitable for sterilization, gamma-ray irradiation under degassing can suppress loss of reaction activity of FGF-2 with an anti-FGF-2 antibody.

A band signal was clearly detected at a position of 17 kDa in the no irradiation group. When the signal intensity in the no irradiation group as a control was 100%, the signal intensities in the irradiation group were (i) 13% in irradiation in the same anaerobic-dry packaging as in Example 1, (ii) 19% in irradiation in degassing packaging, and (iii) 14% in irradiation in nitrogen packing packaging (FIG. 5). Accordingly, it was revealed that γ-ray irradiation in a degassing state or in a nitrogen atmosphere suppressed a decrease of FGF-2 having reaction activity with an anti-FGF-2 antibody and in particular a degassing state showed high protective effect on FGF-2 in γ-ray irradiation as compared with that in a nitrogen atmosphere. Even in a case where FGF-2 having reaction activity with an anti-FGF-2 antibody was decreased to 13% in irradiation in anaerobic-dry packaging, the cell proliferation rate of FGF-2 was comparable with that in the no irradiation group, as described in Example 1.

Example 7

Influence of Temperature in Radiation Sterilization, on Bioactivity of Protein Embedded into Inorganic Salt Solid Titanium pins for external fixation, as a metal for transplantation, were coated with apatite into which FGF-2 was embedded, in the same conditions as in Example 1 and the resultants were subjected to γ-ray irradiation at a dose of 25±0.5 kGy at room temperature and at a low temperature, and how the temperature in the γ-ray irradiation influences on reaction activity with an anti-FGF-2 antibody of FGF-2 was examined.

Co-precipitated ApFGF pins were produced using titanium pins for intracorporeal fixation in the same manner as in Example 1, and sealed and packaged by the same degassing packaging as in Example 6. The pin to be subjected to γ-ray irradiation at a low temperature was subjected to γ-ray irradiation in the coexistence with about 3.8 kg of dry ice, and the pin to be subjected to γ-ray irradiation at room temperature was subjected to γ-ray irradiation without dry ice. The sublimation temperature of dry ice is −78.5° C. at atmospheric air pressure. Accordingly, the temperature of dry ice by itself was a temperature of −78.5° C. or less. The dose of irradiation was the same as in Example 6. Thereafter, FGF-2 supported on the pin after the γ-ray irradiation was detected by western blotting according to the same method as in Example 6.

Figure 6:
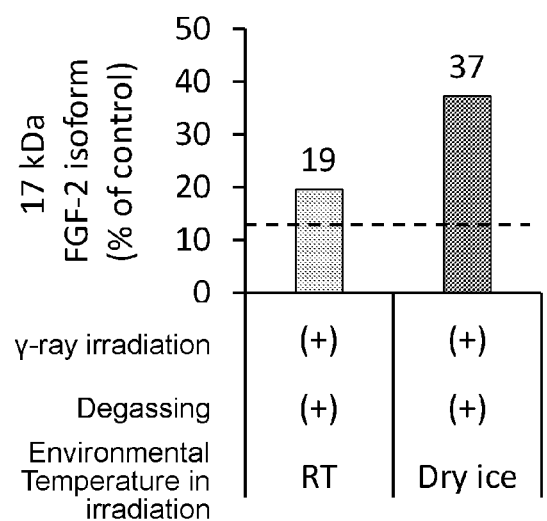
FIG. 6 A graph indicating that, when an external fixation pin made of titanium, for use in bone repair, is coated with FGF-2 embedded into apatite and gamma-ray is irradiated at a dose suitable for sterilization, gamma-ray irradiation not only under degassing, but also at a low temperature in the presence of dry ice can suppress loss of reaction activity of FGF-2 with an anti-FGF-2 antibody.

FIG. 6 illustrates the influence of the temperature in radiation sterilization on FGF-2 of 17 kDa, having reaction activity with an anti-FGF-2 antibody embedded into apatite. Bands were detected at a position of 17 kDa in both groups. It was further revealed that irradiation at a low temperature of around −80° C. by dry ice led to a signal intensity increased twofold as compared with that in irradiation at room temperature (FIG. 6). It was revealed therefrom that γ-ray irradiation at a low temperature in the coexistence of dry ice in addition to degassing packaging suppressed a decrease of FGF-2 having reaction activity with an anti-FGF-2 antibody, and exhibited high protective effect on FGF-2 as compared with γ-ray irradiation at room temperature.

Example 8

Bone Differentiation Promotion Activity after Radiation Sterilization of Apatite Ceramic for Artificial Bone, Coated with Apatite into which Human Recombinant BMP-2(rhBMP-2) was Embedded FGF-2 in Example 1 was changed to rhBMP-2, a dense disc made of apatite was coated with co-precipitated ApBMP and the resultant was subjected to γ-ray irradiation at a dose of 25±0.5 kGy, and the presence of protective effect of BMP-2 against the γ-ray irradiation was examined.

A dense disc made of apatite, produced in the same manner as in Example 4, was used, FGF-2 of Example 4 was changed to human recombinant BMP-2 (rhBMP-2) as an osteogenic protein, and coating with co-precipitated ApBMP was performed. In a control, coating with co-precipitated ApBSA was performed using bovine serum albumin (BSA) instead of rhBMP-2. After the respective apatite discs coated with co-precipitated ApBMP and co-precipitated ApBSA were vacuum-dried and subjected to γ-ray irradiation, rat bone marrow-derived mesenchymal stem cells were seeded on each of the discs, and a bone differentiation marker was measured after 12 days from bone differentiation induction. The mesenchymal stem cells here used were primary mesenchymal stem cells isolated from the bone marrow of a 7-week-old F344/NSlc rat, and the mesenchymal stem cells seeded on each of the discs were cultured in a bone differentiation induction medium to which 10 mMβ glycerophosphate and 0.28 mM ascorbic acid were added, for 12 days soon after seeding, in a condition of no addition or addition of 10 nM dexamethasone (Dex). A half amount of the medium was exchanged every two days. After cultured for 12 days, the cells were frozen and lysed in 0.1% Triron-X-containing PBS, and alkaline phosphatase (ALP) activity as a bone differentiation marker was quantitatively determined using LabAssay ALP (FUJIFILM Wako Pure Chemical Corporation). The amount of DNA in a cell lysate was quantitatively determined using Quant-iT (registered trademark) PicoGreen (registered trademark) dsDNA Reagent and Kits (Thermo Fisher Scientific) in order to evaluate activity per the number of cells.

Figure 7:
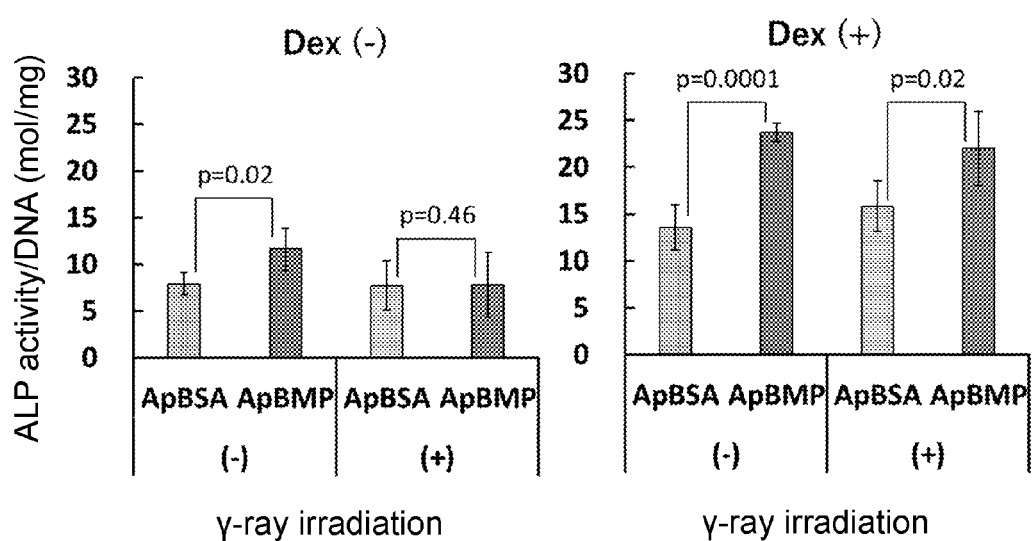
FIG. 7 A graph indicating that, when a disc made of apatite is coated with BMP-2 embedded into apatite and gamma-ray is irradiated at a dose suitable for sterilization, the ability of BMP-2 to induce differentiation of cord mesenchymal stem cells in the presence of Dex remains.

FIG. 7 illustrates the ALP activity per the amount of DNA after differentiation induction in the absence or presence of Dex on a disc made of apatite coated with apatite into which BMP-2 was embedded and subjected to γ-ray irradiation. As illustrated in FIG. 7, the ALP activity per the amount of DNA after differentiation induction in the absence of Dex on a disc made of co-precipitated ApBMP apatite was significantly higher than that of ApBSA in the no γ-ray irradiation group (p=0.02), and comparable with that of ApBSA in the irradiation group (p=0.46). On the other hand, the ALP activity per the amount of DNA after differentiation induction in in the presence of Dex was significantly higher than those of ApBSA in both the γ-ray irradiation group and the no irradiation group (p=0.02, 0.0001). In other words, it was shown that embedding BMP-2 as an osteogenic protein in apatite allows bone differentiation promotion action in the presence of Dex, as one bioactivity of BMP-2, to be maintained even after γ-ray sterilization. In other words, it was revealed that, in a case where a ceramic for transplantation was coated with a composition where BMP-2 was embedded into apatite, ionizing radiation sterilization resistance can be attained by embedding and specific bioactivity of protein can be maintained, as in a case where FGF-2 was embedded into apatite, namely, that embedding into apatite exhibited radioprotective effect on specific bioactivity of protein.

Example 9

Influence of Coexistence of L-Ascorbic Acid Phosphate Magnesium Salt N-Hydrate in Radiation Sterilization, on Bioactivity of Protein Embedded into Inorganic Salt Solid Titanium pins for external fixation, as a metal for transplantation, were coated with apatite into which FGF-2 was embedded, in the same conditions as in Example 1, and immersed in a solution (AsMg solution) of L-ascorbic acid phosphate magnesium salt n-hydrate for several seconds and vacuum-dried. The co-precipitated ApFGF pins produced were subjected to γ-ray irradiation at a dose of 25±0.5 kGy, and how the coexistence of AsMg in the γ-ray irradiation influences on FGF-2 having reaction activity with an anti-FGF-2 antibody was examined.

After titanium pins for intracorporeal fixation were coated with apatite into which FGF-2 was embedded, in the same manner as in Example 1, the resultants were immersed in a 25 mM AsMg solution for several seconds twice, and vacuum-dried, to thereby add AsMg to the apatite into which FGF-2 was embedded. The co-precipitated ApFGF pins produced were sealed and packaged in the same degassing packaging as in Example 6, and subjected to γ-ray irradiation at a dose of 25±0.5 kGy. Thereafter, FGF-2 supported on the pin after the γ-ray irradiation was detected by western blotting according to the same method as in Example 6.

Figure 8:
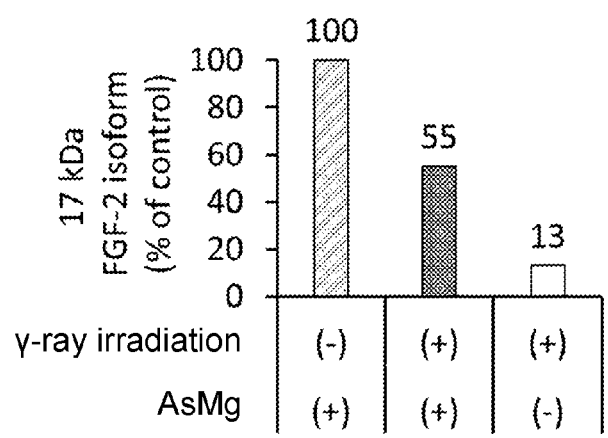
FIG. 8 A graph indicating that, when an external fixation pin made of titanium, for use in bone repair, is coated with FGF-2 embedded into apatite and gamma-ray is irradiated at a dose suitable for sterilization, the addition of ascorbate to the coating can suppress loss of reaction activity of FGF-2 with an anti-FGF-2 antibody after gamm-ray irradiation.

FIG. 8 illustrates the influence of addition of AsMg to apatite into which FGF-2 is embedded, in radiation sterilization, on reaction activity with an anti-FGF-2 antibody of FGF-2 embedded. Bands were detected at a position of 17 kDa in all the groups of no γ-ray irradiation, γ-ray irradiation in the presence of AsMg, and γ-ray irradiation in the absence of AsMg. In a case where the signal intensity in the no irradiation group was 100%, the signal intensity in the γ-ray irradiation group in the presence of AsMg was 55%. However, the signal intensity in the γ-ray irradiation group in the absence of AsMg was 13%, and was a signal intensity about one-fourth of the γ-ray irradiation group in the presence of AsMg. Accordingly, it was revealed that γ-ray irradiation in a condition of addition of AsMg to apatite into which FGF-2 was embedded suppressed a decrease of FGF-2 having reaction activity with an anti-FGF-2 antibody and that, in this condition, protective effect of FGF-2 in γ-ray irradiation was high as compared with that in the absence of AsMg. It is considered that AsMg is one of ascorbic acid compounds having anti-oxidation action and thus excellent protective effect suppresses generation of radical due to radiation irradiation.

Example 10

Cell Proliferation Activity after Radiation Sterilization of External Fixation Titanium Pin Coated with Apatite into or to which not Only FGF-2, but Also Heparin was Embedded or Adsorbed A external fixation titanium pin coated with apatite into which both FGF-2 and heparin were embedded, and an external fixation titanium pin coated with apatite to which both FGF-2 and heparin were adsorbed were produced, these pins were subjected to γ-ray irradiation at a dose of 25±0.5 kGy, and thereafter whether or not FGF-2 had cell proliferation activity was examined.

Sodium heparin was added at a concentration of 0.5 units/ml to an unstable supersaturated calcium phosphate solution to which FGF-2 was added at each of concentrations of 4 μg/ml and 0 μg/ml as in Example 1. External fixation titanium pins (DePuy Synthes, cell drill 4.0/3.0 mm Ti, 20 mm-80 mm) were immersed in these unstable supersaturated calcium phosphate solution in the same conditions as in Example 1, and coated with FGF-2 and heparin co-precipitated together with apatite (co-precipitated ApFGF heparin pin). On the other hand, sodium heparin was added at a concentration of 0.5 units/ml to the supersaturated calcium phosphate solution containing 12 μg/ml of FGF-2 of Example 2. The external fixation titanium pin was immersed in the unstable supersaturated calcium phosphate solution for several seconds in the same conditions as in Example 2, and coated with apatite to which FGF-2 and heparin were adsorbed (adsorbed ApFGF heparin pin). The resultants were vacuum-dried, subjected to γ-ray irradiation or no irradiation, stored, and evaluated with respect to the cell proliferation activity in the same conditions as in Example 1.

Table 6 shows the number of co-precipitated or adsorbed ApFGF heparin pins rated as "having activity" in three repeated trials.

TABLE 6

| Number of trials | External fixation titanium pin | | | |
|---|---|---|---|---|
| | Co-precipitated ApFGF/heparin | | Adsorbed ApFGF/heparin | |
| | γ-ray (−) | (+) | (−) | (+) |
| First trial | 3/3 | 3/3 | 3/3 | 3/3 |
| Second trial | 3/3 | 3/3 | 3/3 | 0/3 |
| Third trial | 3/3 | 3/3 | 3/3 | 0/3 |
| Total (pins) | 9/9 | 9/9 | 9/9 | 3/9 |

As shown in Table 6, 9 pins/9 pins in the γ-ray irradiation group of the co-precipitated ApFGF heparin pins, and 9 pins/9 pins in the no irradiation group thereof were rated as "having cell proliferation activity", and the number of pins having cell proliferation activity was the same between the γ-ray irradiation group and the no irradiation group, in the three trials. On the other hand, 3 pins/9 pins in the γ-ray irradiation group of the adsorbed ApFGF heparin pins, and 9 pins/9 pins in the no irradiation group thereof were rated as "having cell activity", and the number of pins having cell proliferation activity in the γ-ray irradiation group was about one-third of the no irradiation group. Both the groups were subjected to the chi-square test, and a significant difference (p=0.003) was recognized between the γ-ray irradiation group and the no irradiation group. In other words, it was revealed that the adsorbed ApFGF heparin pin more strongly tended to lose bioactivity of FGF-2 by γ-ray irradiation sterilization.

Figure 9:
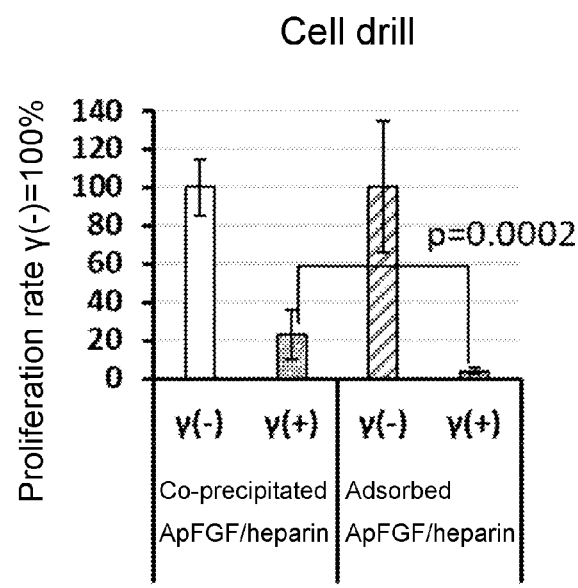
FIG. 9 A graph indicating that, when a coating layer in which both FGF-2 and heparin are embedded into apatite and a coating layer in which both FGF-2 and heparin are adsorbed to apatite are each produced on an external fixation pin made of titanium and subjected to gamma-ray irradiation at a dose suitable for sterilization and thereafter the respective cell proliferation activities of FGF-2 thereof are compared, the coating layer in which both FGF-2 and heparin are embedded into apatite can suppress loss of cell proliferation activity of FGF-2 than the coating layer in which both FGF-2 and heparin are adsorbed to apatite.

As illustrated in FIG. 9, the cell proliferation rate in the γ-ray irradiation group, normalized under the assumption that the cell proliferation rate in the no γ-ray irradiation group was 100%, was about 23% with respect to the co-precipitated ApFGF heparin pin, but was as slight as 4% with respect to the adsorbed ApFGF heparin pin, and there was a statistically significant difference (p=0.0002) between both the values. In other words, it was revealed that the intracorporeal fixation pin made of titanium as a metal for transplantation, coated with the composition in which both FGF-2 and heparin were embedded into apatite, had higher ionizing radiation sterilization resistance than that coated with apatite to which both FGF-2 and heparin were adsorbed, namely, radioprotective effect was exhibited in a case where not only the protein having bioactivity, but also heparin having no bioactivity was further embedded into apatite.

Example 11

Comparison of Cell Proliferation Activity after Radiation Sterilization Between External Fixation Titanium Pin Coated with Apatite into which FGF-2 was Embedded and External Fixation Titanium Pin Coated with Apatite into which both FGF-2 and Heparin were Embedded The cell proliferation rate of the co-precipitated ApFGF pin of Example 1 and the cell proliferation rate after radiation sterilization of the co-precipitated ApFGF heparin pin of Example 10 were compared to examine the effect of embedding of heparin in addition to FGF-2.

In Example 1, a dissolution liquid produced by dissolving a coating layer on the co-precipitated ApFGF pin after radiation sterilization, in a 10 mM sodium citrate solution, was added to mouse fibroblast strain NIH3T3, and the cell proliferation rate was quantitatively evaluated. As a result, the value of the cell proliferation rate was 1.53±0.27 (FIG. 1). On the contrary, in a case where a dissolution liquid produced by dissolving a coating layer on the co-precipitated ApFGF heparin pin after radiation sterilization, in a 10 mM sodium citrate solution, was added to mouse fibroblast strain NIH3T3, the cell proliferation rate was high to such an extent as to exceed the quantitation limit. The dissolution liquid was here diluted by 30-fold and added to mouse fibroblast strain NIH3T3, the cell proliferation rate was quantitatively evaluated, and thereby 1.67±0.07 was obtained as a value of the cell proliferation rate. In other words, it was indicated that when polysaccharide such as heparin which was derived from an extracellular matrix and which had, by itself, no direct cell proliferation/differentiation activity was embedded together with a bioactive protein, higher bioactivity after radiation sterilization can be maintained at a higher level.

Example 12

Cell Proliferation Activity after Radiation Sterilization of Zirconia for Artificial Joint-Artificial Bone, Coated with Apatite into or to which not Only FGF-2, but Also Heparin was Embedded or Adsorbed Zirconias for artificial joint-artificial bone, coated with apatite into which both FGF-2 and heparin were embedded, and zirconias for artificial joint-artificial bone, coated with apatite to which both FGF-2 and heparin were adsorbed were produced, and these were subjected to γ-ray irradiation at a dose of 25±0.5 kGy, and thereafter whether or not FGF-2 had cell proliferation activity was examined.

A zirconia square bar (2.4 mm×2.4 mm×21 mm) was coated, vacuum-dried, subjected to γ-ray irradiation or no irradiation, stored, and measured with respect to the cell proliferation rate in the same conditions as in Example 10.

Table 7 shows the number of zirconia bars with co-precipitated ApFGF/heparin or adsorbed, rated as "having activity", in two repeated trials.

TABLE 7

| Number of trials | Zirconia | | | |
|---|---|---|---|---|
| | Co-precipitated ApFGF/heparin | | Adsorbed ApFGF/heparin | |
| | γ-ray (−) | (+) | (−) | (+) |
| First trial | 3/3 | 3/3 | 3/3 | 0/3 |
| Second trial | 3/3 | 3/3 | 3/3 | 2/3 |
| Total (bars) | 6/6 | 6/6 | 6/6 | 2/6 |

As shown in Table 7, 6 bars/6 bars in the γ-ray irradiation group of the zirconia bars with co-precipitated ApFGF/heparin, and 6 bars/6 bars in the no irradiation group thereof were rated as "having cell activity", and the number of such zirconia bars having cell proliferation activity was the same between the γ-ray irradiation group and the no irradiation group, in the two trials. On the other hand, 2 bars/6 bars in the γ-ray irradiation group of the zirconia bars with adsorbed ApFGF/heparin, and 6 bars/6 bars in the no irradiation group thereof were rated as "having cell activity", and the number of such pins each having cell proliferation activity in the γ-ray irradiation group was about one-third of the no irradiation group. Both the groups were subjected to the chi-square test, and a significant difference (p=0.014) was recognized between the γ-ray irradiation group and the no irradiation group. In other words, it was revealed that the zirconia with adsorbed ApFGF/heparin more strongly tended to lose bioactivity of FGF-2 by γ-ray irradiation sterilization.

Figure 10:
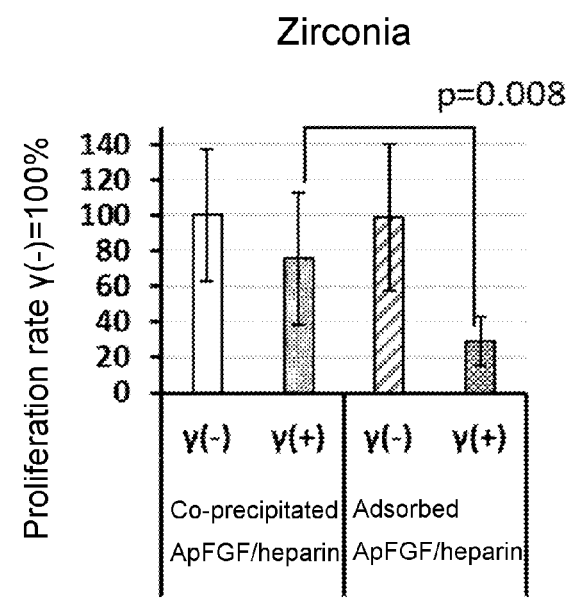
FIG. 10 A graph indicating that, in a case where a coating layer in which both FGF-2 and heparin are embedded into apatite and a coating layer in which both FGF-2 and heparin are adsorbed to apatite are each produced on zirconia for artificial joint and artificial bone and subjected to gamma-ray irradiation at a dose suitable for sterilization and thereafter the respective cell proliferation activities of FGF-2 thereof are compared, the coating layer in which both FGF-2 and heparin are embedded into apatite can suppress loss of cell proliferation activity of FGF-2 than the coating layer in which both FGF-2 and heparin are adsorbed to apatite.

As illustrated in FIG. 10, the cell proliferation rate in the γ-ray irradiation group, normalized under the assumption that the cell proliferation rate in the no γ-ray irradiation group was 100%, was about 76% with respect to the zirconia with co-precipitated ApFGF/heparin, but was as slight as 29% with respect to the zirconia with adsorbed ApFGF/heparin, and there was a statistically significant difference (p=0.008) between both the values. In other words, it was revealed that the zirconia as a ceramic for transplantation, coated with the composition in which both FGF-2 and heparin were embedded into apatite, had higher ionizing radiation sterilization resistance than that coated with apatite to which both FGF-2 and heparin were adsorbed, namely, radioprotective effect was exhibited in a case where not only the protein having bioactivity, but also heparin having no bioactivity was further embedded into apatite.

Example 13

Compositional Analysis of Coating Layer after Radiation Sterilization of External Fixation Pin Coated with Apatite into which FGF-2 was Embedded The co-precipitated ApFGF pins in γ-ray irradiation and no irradiation, produced in Example 1, and the adsorbed ApFGF pins in γ-ray irradiation and no irradiation, produced in Example 2, were each immersed in a 10 mM sodium citrate solution for 30 minutes, and co-precipitated ApFGF and adsorbed ApFGF each serving as the coating layer were each lysed. Each lysate was chemically analyzed by an ICP emission spectrometric analysis method, and each amount of calcium and phosphorus in the co-precipitated ApFGF and the adsorbed ApFGF was quantitatively determined. The results are shown in Table 8.

TABLE 8

| | Co-precipitated ApFGF pin | | Adsorbed ApFGF pin | |
|---|---|---|---|---|
| | γ-ray (−) | (+) | (−) | (+) |
| Ca (µg/pin) | 195.1 ± 8.0 | 204.6 ± 6.2 | 232.6 ± 11.9 | 250.9 ± 25.5 |
| P (µg/pin) | 88.6 ± 2.9 | 92.3 ± 3.1 | 102.9 ± 5.4 | 110.1 ± 10.1 |
| Ca/P molar ratio | 1.70 ± 0.01 | 1.71 ± 0.02 | 1.75 ± 0.01 | 1.76 ± 0.02 |

It was indicated from Table 8 that the co-precipitated ApFGF serving as the coating layer included calcium phosphate as a main component. The Ca/P molar ratio (1.70 to 1.71) in the co-precipitated ApFGF was a value close to the theoretic Ca/P molar ratio (1.67) of apatite ($Ca_{10}(PO_4)_6(OH)_2$) including no impurity element. It is known that in a case where a phosphate group of apatite is replaced with any of impurities, a Ca/P molar ratio will be more than 1.67, and representative impurities with which the phosphate group is replaced include a carbonate group. Since the co-precipitated ApFGF of Example 1 and Example 2 were produced in a solution containing carbonate ion, it was considered that apatite containing a carbonate group was co-precipitated together with FGF-2 to embed FGF-2 thereinto or apatite and calcium carbonate were co-precipitated together with FGF-2 to embed FGF-2 thereinto.

Example 14

Production in Ca—$PO_4$—K—Na—Cl-Based Unstable Supersaturated Calcium Phosphate Solution An unstable supersaturated calcium phosphate solution was used which included 1.00 mM of Ca ion, 1.00 mM of phosphate ion, 2.00 mM of K ion, 16.7 mM of Na ion, 2.00 mM of Cl ion, and 16.7 mM of $HCO_3$ ion, which had a pH of 8.3, and in which calcium phosphate would be crystallized by spontaneous nucleation in about 4 to 5 hours if left at 37° C. Zirconias with co-precipitated ApFGF/heparin were produced in the completely same conditions as in Example 12 except that the immersion time was 24 hours, and the resultants were vacuum-dried, subjected to γ-ray irradiation, stored, and measured with respect to the cell proliferation rate.

Table 9 shows the number of zirconias with co-precipitated ApFGF/heparin, rated as "having activity".

TABLE 9

| | Zirconia with co-precipitated ApFGF/heparin | |
|---|---|---|
| | γ-ray (−) | (+) |
| Number of zirconias rated as "having activity" | 3/3 | 3/3 |

As shown in Table 9, 3 zirconias/3 zirconias in the γ-ray irradiation group of the zirconias with co-precipitated ApFGF/heparin, and 3 zirconias/3 zirconias in the no irradiation group thereof were rated as "having cell activity", and the number of zirconias having cell proliferation activity was the same between the γ-ray irradiation group and the no irradiation group. In other words, it was revealed that, also in a case where a Ca—$PO_4$—K—Na—Cl-based unstable supersaturated calcium phosphate solution was used to coat zirconia as a ceramic for transplantation with the composition in which both FGF-2 and heparin were embedded into apatite, embedding into apatite exhibited the radioprotective effect.

Example 15

Analysis of Coating Layer of Zirconia Coated with Apatite into which Both FGF-2 and Heparin were Embedded The co-precipitated ApFGF heparin coating layers produced in Example 14 were subjected to compositional analysis by the same method as in Example 13. The co-precipitates in production of the zirconia with co-precipitated ApFGF/heparin in Example 14 were placed on a silicon non-reflective plate, and analyzed by a powder X-ray diffraction method. Powder X-ray diffraction was performed using CuKα rays in conditions of 40 kV and 100 mA. The results of compositional analysis are shown in Table 10.

TABLE 10

| | Zirconia with co-precipitated ApFGF/heparin | |
|---|---|---|
| | γ-ray (−) | (+) |
| Ca (μg/pin) | 5.11 ± 0.21 | 5.50 ± 0.38 |
| P (μg/pin) | 2.25 ± 0.06 | 2.59 ± 0.30 |
| Ca/P molar ratio | 1.76 ± 0.06 | 1.65 ± 0.14 |

It was indicated from Table 10 that the co-precipitated ApFGF serving as a coating layer included calcium phosphate. The Ca/P molar ratio in the co-precipitated ApFGF was 1.70 to 1.82 in the no γ-ray irradiation group and was 1.51 to 1.79 in the irradiation group.

It was considered from the Ca/P ratio that FGF-2 and heparin were embedded into carbonate group-containing apatite or FGF-2 and heparin were embedded into apatite and calcium carbonate, as in Example 13. Furthermore, because the Ca/P molar ratio of amorphous calcium phosphate is typically 1.5, it was also indicated that amorphous calcium phosphate was to be deposited.

Figure 11:
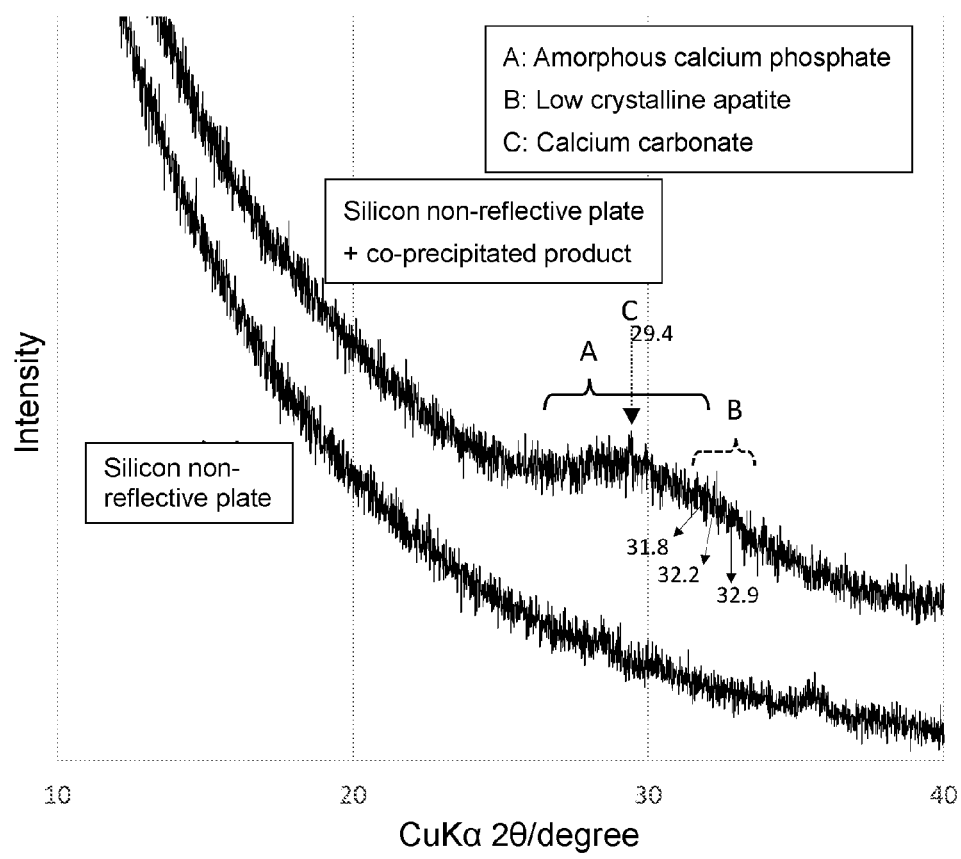
FIG. 11 A graph represents a powder X-ray diffraction pattern which indicates that a co-precipitated product in production of a coating layer in which both FGF-2 and heparin are embedded into apatite, on zirconia, is an inorganic salt solid containing low crystalline apatite, amorphous calcium phosphate, and calcium carbonate, as main components.

FIG. 11 represents the results of analysis by a powder X-ray diffraction method. It is known that amorphous calcium phosphate appears as a broad peak large in half-value width at around 30°. As illustrated in FIG. 11, a broad peak large in half-value width, corresponding to amorphous calcium phosphate, was confirmed at around 30° in a powder X-ray diffraction pattern of the co-precipitate. Three strong diffraction lines ((211), (112), (300)) characteristic of crystalline apatite, appearing at 31.8°, 32.2°, and 32.9°, were not separated, and formed one broad peak at around 32°. Accordingly, the apatite as the co-precipitate was a low crystalline apatite. Additionally, a peak of calcium carbonate was observed at 29.4°. In other words, the co-precipitated product contains amorphous calcium phosphate, low crystalline apatite, and calcium carbonate as main components. The co-precipitated product does not include crystalline apatite with low solubility, but includes amorphous calcium phosphate, low crystalline apatite, and calcium carbonate each having relatively high solubility, as main components, and is suitable for gradually releasing protein embedded.

INDUSTRIAL APPLICABILITY

The medical instrument of the present invention, in which an inorganic salt solid such as apatite, into which a protein having bioactivity, such as a growth factor, is embedded, is placed so as to coat a metal or ceramic therewith, allows deactivation of bioactivity of the protein due to radiation sterilization to be suppressed, and therefore a simple terminal sterilization method by radiation can be applied to various processes for producing a medical instrument utilizing the bioactivity of the protein and an aseptic production method can be avoided, resulting in a significant decrease in cost.

The invention claimed is:

1. A method for producing a medical instrument for use in mammals including human beings, comprising a step of coating a part or entirety of a substance with a crystalline or an amorphous inorganic salt into which a protein having bioactivity and heparin are embedded, and a step of exposing the coated substance to a gamma ray and/or an electron beam at a dose sufficient for sterilization in a condition where generation of radical is suppressed, wherein,
the substance is a metal, a ceramic, or both,
the inorganic salt is at least one inorganic salt selected from the group consisting of apatite, tricalcium phosphate, octacalcium phosphate, amorphous calcium phosphate, and calcium carbonate, and
the condition is a degassing state at an atmospheric pressure of 50 kPa or less.

2. The method according to claim 1, wherein the metal is at least one metal selected from the group consisting of titanium, a titanium alloy, stainless steel, and a cobalt/chromium alloy.

3. The method according to claim 1, wherein the ceramic is at least one ceramic selected from the group consisting of apatite, tricalcium phosphate, octacalcium phosphate, amorphous calcium phosphate, alumina, zirconia, and a composite thereof.

4. The method according to claim 1, wherein the dose of the gamma ray is 3 kGy to 40 kGy.

5. The method according to claim 1, wherein the protein is a growth factor.

6. The method according to claim 5, wherein the growth factor is FGF-2.

* * * * *